United States Patent [19]

Tanikawa et al.

[11] Patent Number: 5,202,323
[45] Date of Patent: Apr. 13, 1993

[54] 5 ARYLMETHYLAMINO 6 OXY SUBSTITUTED 3(2H)-PYRIDAZINONES

[75] Inventors: Keizo Tanikawa; Akira Saito; Takashi Matsumoto; Ryozo Sakoda, all of Funabashi; Nobutomo Tsuruzoe; Ken-ichi Shikada, both of Shiraoka, all of Japan

[73] Assignee: Nissan Chemical Industries Ltd., Tokyo, Japan

[21] Appl. No.: 768,182

[22] PCT Filed: Apr. 19, 1991

[86] PCT No.: PCT/JP91/00517

§ 371 Date: Oct. 16, 1991

§ 102(e) Date: Oct. 16, 1991

[87] PCT Pub. No.: WO91/16314

PCT Pub. Date: Oct. 31, 1991

[30] Foreign Application Priority Data

Apr. 25, 1990 [JP] Japan ................... 2-109914

[51] Int. Cl.$^5$ ................ A61K 31/50; C07D 237/16
[52] U.S. Cl. ................. 514/236.5; 514/212; 514/247; 514/252; 540/598; 544/114; 544/238; 544/240
[58] Field of Search ............ 514/252, 247, 236.5; 544/240, 238, 114

[56] References Cited

U.S. PATENT DOCUMENTS 4,097,592  6/1978  Hofer et al. ............. 544/240
4,978,665  12/1990  Tanikawa et al. ......... 544/239
5,011,839  4/1991  Tanikawa et al. ......... 514/252
5,034,391  7/1991  Blaschke et al. ......... 514/252

FOREIGN PATENT DOCUMENTS 63-301870  12/1988  Japan .
2-256668   10/1990  Japan .
91-16314   10/1991  PCT Int'l Appl. .

OTHER PUBLICATIONS

Burger ed., "Medicinal Chemistry" 2nd Edition Interscience, N.Y. (1960) p. 42.
Ferlux, Chem. Abstr. vol. 77 entry 88522v.
Craloyan et al. Chem. Abstr. vol. 75 entry 140758b (1971).
K. Buler and D. Pearson "Organic Synthesis", Moscow, Mir Publishers, 1973, vol. 2, pp. 433–434 (fragment).

Primary Examiner—Donald G. Daus
Attorney, Agent, or Firm—Oblon, Spivak, McClelland, Maier & Neustadt

[57] ABSTRACT

A compound of the formula, or its pharmaceutically acceptable salt, and its preparation process and pharmaceutical compositions characterized by containing these compounds as effective ingredients.

These compounds have strong antithrombotic activity, cardiotonic activity, vasodilator activity and anti-SRS-A activity, and are useful as prophylactic or therapeutic agents for various thrombotic affections, congestive heart failure, hypertension, asthma, immediate type allergy diseases and the like.

8 Claims, No Drawings

5 ARYLMETHYLAMINO 6 OXY SUBSTITUTED 3(2H)-PYRIDAZINONES

TECHNICAL FIELD

The present invention relates to novel 3(2H)-pyridazinone derivatives and their pharmaceutically acceptable salts having an inhibitory activity of platelet aggregation, a cardiotonic activity, a vasodilating activity and an anti-SRS-A activity, processes for their preparation and pharmaceutical compositions containing them as active ingredients.

BACKGROUND ART

1) Field of anti-thrombotic agent

It is known that platelet aggregation plays an important role for thrombus formation in connection with a disease state. Various thrombotic diseases caused by thrombus formation mainly include cerebral thrombosis, pulmonal thrombosis, myocardial infarction, angina pectoris, occlusion of peripheral artery and the like, and all of these diseases require development for useful drugs. As a prophylactic or therapeutic drug, an anti-thrombotic agent having an inhibitory activity of platelet aggregation draws public tension. Heretofore, the effect of aspirin has been widely studied, and more recently ticlopidine and cilostazol have been clinically developed. However, a more strongly effective drug is demanded in respect of its effects.

In addition to the above-mentioned various thrombotic diseases, there are enumerated various diseases in relation to platelets. Examples for these diseases include nephritis, cancer cell metastasis and the like, and recently various studies have been conducted with regard to prophylactic or therapeutic effects for these diseases achieved mainly by an anti-thrombotic agent having an activity for controlling platelet function ("Journal of Royal College of Physicians", Vol. 7, No. 1, p. 5–18, 1972; "Japan Clinics (Nihon Rinsho)", Vol. 4, No. 6, p. 130–136, 1988; Anticancer Research, Vol 6, p. 543–548, 1986).

2) Field of cardiotonic agent

A cardiotonic agent to enhance myocardial contractive force have been used as a therapeutic drug for congestive heart failure from old times. However, conventional cardiotonic agents such as cardiac glycosides represented by digitalis, aminophylline and catecholamines have strong side effects, and therefore drugs such as milrinone and denopamine are recently clinically developed.

3) Field of vasodilator

There are many known vasodilators, but at present there are few drugs which have beneficial pharmacologic properties for circulatory system such as a satisfactory inhibitory activity of platelet aggregation.

4) Field of anti-SRS-A agent

SRA-A (Slow Reacting Substances of Anaphylaxis) is a chemical mediator released together with histamine, etc. by an allergic reaction and has pharmacological activity to cause a strong and prolonged contraction of tracheal smooth muscle. Their existence has long been known from such a phenomenal aspect.

It was found in 1979 that SRS-A itself is a mixture of leukotriene $C_4$ (hereinafter referred to as $LTC_4$), leukotriene $D_4$ (hereinafter referred to as $LTD_4$) and leukotriene $E_4$ (hereinafter referred to as $LTE_4$) [generally called peptide leukotriene].

Extensive researches have been conducted on SRS-A for its relationship with a disease state. As a result, the relationship of SRS-A with immediate type allergic diseases such as bronchial asthma, allergic rhinitis, urticaria and hay fever, has become clear.

Further, the relationship of SRS-A with various inflammatory diseases, ischemic heart diseases, etc., has been suggested.

Therefore, a compound which exhibits inhibition against SRS-A, is expected to be useful as a prophylactic or therapeutic drug against the disorders caused by either $LTC_4$, $LTD_4$ or $LTE_4$, or by a mixture thereof.

As the SRS-A antagonists, many medicinal substances have been reported. ("Drugs of the Future", Vol. 12, p. 453–474 (1987); "Annual Reports in Medicinal Chemistry", Vol. 22, p. 73–84 (1987) and "Annual Reviews in Pharmacological Toxicology", Vol. 29, p. 123–143 (1989)).

However, no instance of their practical clinical application has been reported.

Now, the relationship of 6-ω-substituted alkyloxy3(2H)-pyridazinones of the formula [I] and their pharmaceutically acceptable salts thereof according to the present invention with compounds disclosed in published references will be described.

(a) German Laid Open Patent Application No. 1,670,169 (hereinafter referred to as reference (a)) discloses 3(2H)-pyridazinones having hydrogen or an aliphatic, cycloaliphatic, araliphatic or aromatic group at 2-position, chlorine or bromine at 4-position, an aralkylamino group at 5-position, and chlorine, bromine, a hydroxy or $C_1$-$C_4$ alkoxy group at 6-position.

This reference (a) discloses a process for the synthesis of 3(2H)-pyridazinone derivatives, their application to agricultural chemicals, their application as intermediates for medicines or dyestuffs, or their application as intermediates for various compounds. However, no mention is made to their pharmacological activities, and no specific examples are given for such compounds. Further, such compounds are not specifically described.

(b) Japanese Unexamined Patent Publication No. 183675/1983 (hereinafter referred to as reference (b)) discloses 3(2H)-pyridazinone derivatives having a lower alkyl group at the 2-position, a hydrogen atom at the 4-position, a substituted or non-substituted anilino group at the 5-position and a hydroxyl group or a lower alkoxy group at the 6-position.

The 3(2H)-pyridazinone derivatives are disclosed to have analgesic action, anti-inflammatory action, anti-allergic action and anti-rheumatic action, but there is no disclosure concerning pharmacological activities. (c) Japanese Unexamined Patent Publication No. 30187/1988 (which corresponds to U.S. Pat. No. 4,978,665), European Laid Open Patent Publication No. 0275997 (hereinafter referred to as reference (c)) discloses 6-substituted alkoxy-5-substituted benzylamino(2H)-pyridazinone derivatives and their use as an anti-SRS-A agent, which are relatively similar to the compounds of the present invention.

DISCLOSURE OF THE INVENTION

As the result of the extensive study, the present inventors have discovered that the 3(2H)-pyridazinone derivatives and their pharmaceutically acceptable salts of the present invention, which are different from any of the compounds disclosed in the above references (a)–(c), are excellent compounds for anti-thrombotic agents, cardiotonic agents, vasodilators and/or anti- SRS-A agents, and that they can be active ingredients of prophylactic or therapeutic drugs for the above-mentioned various thrombotic diseases, congestive heart failure, hypertension and/or asthma or immediate type allergy diseases. On the basis of this discovery, the present invention has been accomplished.

That is, the present invention relates to a 3(2H)-pyridazinone derivative and its pharmaceutically acceptable salt, a process for producing the same and a pharmaceutical composition containing the same as an active ingredient, the 3(2H)-pyridazinone derivative being represented by the general formula [I],

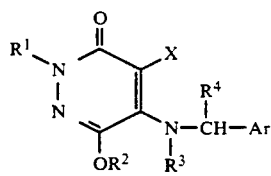
[I]

wherein $R^1$ is a hydrogen atom, a straight chained or branched $C_1-C_4$ alkyl group, a $C_3-C_4$ alkenyl group or $(CH_2)_nCO_2R^5$ (n is an integer of from 1 to 4, $R^5$ is a hydrogen atom or a straight chained or branched $C_1-C_4$ alkyl group);

$R^2$ is $A^1-Y^1$ [$A^1$ is a straight chained or branched $C_1-C_{12}$ alkylene group, $Y^1$ is $CO_2R^5$ ($R^5$ is as defined above), a cyano group, $OR^6$ ($R^6$ is a hydrogen atom, a straight chained or branched $C_1-C_4$ alkyl group or a phenyl group), or a thienyl or pyridyl group which may be substituted at any position,

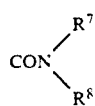

($R^7$ and $R^8$ are respectively and independently a hydrogen atom, a straight chained or branched $C_1-C_4$ alkyl group, a $C_3-C_8$ cycloalkyl group, a phenyl group or a thiazolyl or thiadiazolyl group which may be substituted at any position, or $R^7$ and $R^8$ together form a $C_2-C_8$ alkylene group which may be substituted with a straight chained or branched $C_1-C_3$ alkyl group or a phenyl group, or form a morpholine ring with a nitrogen atom),

($R^5$ is as defined above, $R^9$ is a straight chained or branched $C_1-C_4$ alkyl group or a phenyl group which may be substituted with a straight chained or branched $C_1-C_4$ alkyl group or a halogen atom),

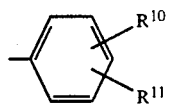

($R^{10}$ and $R^{11}$ are respectively and independently a hydrogen atom, a halogen atom, a straight chained or branched $C_1-C_4$ alkyl group, a $C_1-C_4$ acylamino group, $OR^5$ ($R^5$ is as defined above), $NHSO_2R^9$ ($R^9$ is as defined above) or $S(O)_m-R^{12}$ (m is an integer of from 0 to 2 and $R^{12}$ is a straight chained or branched $C_1-C_4$ alkyl group), provided that $R^{10}$ and $R^{11}$ are not hydrogen atoms at the same time),

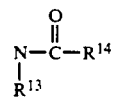

($R^{13}$ is a hydrogen atom, $R^{14}$ is a phenyl group, or $R^{13}$ and $R^{14}$ together form a $C_2-C_8$ alkylene group which may be substituted with a straight chained $C_1-C_3$ alkyl group),

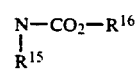

($R^{15}$ is a hydrogen atom or a straight chained or branched $C_1-C_4$ alkyl group, $R^{16}$ is a straight chained or branched $C_1-C_4$ alkyl group, or $R^{15}$ and $R^{16}$ together form a $C_2-C_8$ alkylene group which may be substituted with a straight chained $C_1-C_3$ alkyl group),

($R^{17}$ and $R^{18}$ are respectively and independently a straight chained or branched $C_1-C_4$ alkyl group, or $R^{17}$ and $R^{18}$ together form a $C_2-C_8$ alkylene group which may be substituted with a straight chained $C_1-C_3$ alkyl group),

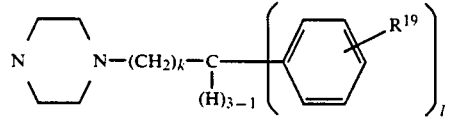

(l is 1 or 2, k is an integer of from 0 to 3, and $R^{19}$ is a hydrogen atom or a halogen atom), or

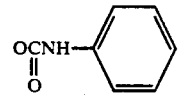

]; or $R^2$ is $A^2-Y^2$ ($A^2$ is a $C_2-C_{10}$ alkylene group which may be substituted with a straight chained $C_1-C_3$ alkyl group, except for the case that a carbon chain connecting an oxygen atom with $Y^2$ has one carbon, and $Y^2$ is a phenyl group);

$R^3$ and $R^4$ are respectively and independently a hydrogen atom or a straight chained or branched $C_1-C_3$ alkyl group;

X is a chlorine atom, a bromine atom, a hydrogen atom or a cyano group; and

Ar is

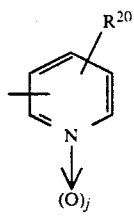

[j is 0 or 1 and $R^{20}$ is a hydrogen atom, a halogen atom or $OR^{12}$ ($R^{12}$ is as defined above)],

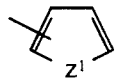

($Z^1$ is an oxygen atom or a sulfur atom),

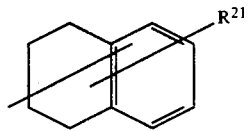

[$R^{21}$ is a hydrogen atom or $OR^5$ ($R^5$ is as defined above)], or

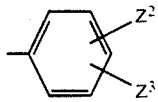

[$Z^2$ and $Z^3$ are respectively and independently a hydrogen atom, a halogen atom, a straight chained or branched $C_1$–$C_4$ alkyl group, $OR^{22}$ ($R^{22}$ is a hydrogen atom or a straight chained or branched $C_1$–$C_8$ alkyl group), or $O$—$A^1$—$Y^3$ ($A^1$ is as defined above and $Y^3$ is a phenyl group which may be substituted with a straight chained or branched $C_1$–$C_4$ alkyl group or a halogen atom, $CO_2R^5$, or

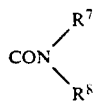

($R^5$, $R^7$ and $R^8$ are as defined above)), or $Z^2$ and $Z^3$ together with a benzene ring, form

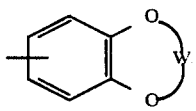

(W forms a $C_1$–$C_8$ alkylene group which may be substituted with a straight chained $C_1$–$C_3$ alkyl group)]}; and a pharmaceutically acceptable salt thereof.

$R^1$, $R^2$, $R^3$, $R^4$, X and Ar in the above general formula [I] representing the compound of the present invention are explained hereinafter.

Examples of $R^1$ include, a hydrogen atom, a methyl group, an ethyl group, an n-propyl group, an i-propyl group, an n-butyl group, an i-butyl group, a sec-butyl group, a t-butyl group, a 2-propenyl group, a 2-methyl-2-propenyl group, a carboxymethyl group, a 2-carboxyethyl group, a 3-carboxypropyl group, a 4-carboxybutyl group, a methoxycarbonylmethyl group, a 2-methoxycarbonylethyl group, a 3-methoxycarbonylpropyl group, a 4-methoxycarbonyl butyl group, an ethoxycarbonylmethyl group, a 2-ethoxycarbonylethyl group, a 3-ethoxycarbonylpropyl group, a 4-ethoxycarbonylbutyl group, an n-propoxycarbonylmethyl group, an i-propoxycarbonylmethyl group, a 2-n-propoxycarbonylethyl, a 2-i-propoxycarbonylethyl group, a 3-n-propoxycarbonylpropyl group, a 3-i-propoxycarbonylpropyl group, a 4-n-propoxycarbonylbutyl group, a 4-i-propoxycarbonylbutyl group, an n-butoxycarbonylmethyl group, an i-butoxycarbonylmethyl group, a sec-butoxycarbonylmethyl group, a t-butoxycarbonylmethyl group, a 2-n-butoxycarbonylethyl group, a 2-i-butoxycarbonylethyl group, a 2-sec-butoxycarbonylethyl group, a 2-t-butoxycarbonylethyl group, a 3-n-butoxycarbonylpropyl group, a 3-i-butoxycarbonylpropyl group, a 3-sec-butoxycarbonylpropyl group, a 3-t-butoxycarbonylpropyl group, a 4-n-butoxycarbonylbutyl group, a 4-i-butoxycarbonylbutyl group, a 4-sec-butoxycarbonylbutyl group, a 4-t-butoxycarbonylbutyl group and the like, preferably a hydrogen atom, an ethyl group and an i-propyl group, and more preferably a hydrogen atom.

Examples of $R^2$ include $A^1$-$Y^1$ or $A^2$-$Y^2$ wherein $A^1$ is a straight chained or branched $C_1$–$C_{12}$ alkylene group and $A^2$ is a $C_2$–$C_{10}$ alkylene group which may be substituted with a straight chained $C_1$–$C_3$ alkyl group, except for the case that a carbon chain connecting an oxygen atom with $Y^2$ has one carbon atom.

Examples of $Y^1$ include a carboxyl group, a methoxycarbonyl group, an ethoxycarbonyl group, an n-propoxycarbonyl group, an i-propoxycarbonyl group, an n-butoxycarbonyl group, an i-butoxycarbonyl group, a sec-butoxycarbonyl group, a t-butoxycarbonyl group, a 2-thienyl group, a 3-thienyl group, a 2-pyridyl group, a 3-pyridyl group, a 4-pyridyl group, a cyano group, a hydroxyl group, a methoxy group, an ethoxy group, an n-propoxy group, an i-propoxy group, an n-butoxy group, an i-butoxy group, a sec-butoxy group, a t-butoxy group, a phenoxy group, a carbamoyl group, an N-methylaminocarbonyl group, an N-ethylaminocarbonyl group, an N-n-propylaminocarbonyl group, an N-i-propylaminocarbonyl group, an N-n-butylaminocarbonyl group, an N-i-butylaminocarbonyl group, an N-sec-butylaminocarbonyl group, an N-t-butylaminocarbonyl group, an N-cyclopropylaminocarbonyl group, an N-cyclobutylaminocarbonyl group, an N-cyclopentylaminocarbonyl group, an N-cyclohexylaminocarbonyl group, an N-cycloheptylaminocarbonyl group, an N-cyclooctylaminocarbonyl group, an N-phenylaminocarbonyl group, an N-2-thiazolylaminocarbonyl group, an N-4-thiazolylaminocarbonyl group, an N-5-thiazolylaminocarbonyl group, an N-2-thiadiazolylaminocarbonyl group, an N-5-thiadiazolylaminocarbonyl group, a 1-aziridinocarbonyl group, a 1-azetidinocarbonyl group, a 1-pyrrolidinocarbonyl group, a 1-piperidinocarbonyl group, a 1-homopiperidinocarbonyl group, a 1-(2,5-dimethyl)-pyrrolidinocarbonyl group, a 1-(2,6-dimethyl)-piperidinocarbonyl group, a 1-(3-phenyl)pyrrolidinocarbonyl group, a 1-(4-phenyl)piperidinocarbonyl group, an N-methylsulfonylamino group, an N-ethylsulfonylamino group, an N-n-propylsulfonyl group, an N-i-propylsulfonylamino group, an N-n- butylsulfonylamino group, an N-i-butylsulfonylamino group, an N-sec-butylsulfonylamino group, an N-t-butylsulfonylamino group, a 1-morpholinocarbonyl group, an N-phenylsulfonylamino group, an N-substituted phenylsulfonylamino group (which is substituted with a methyl group, an ethyl group, an n-propyl group, an i-propyl group, an n-butyl group, an i-butyl group, a sec-butyl group, a t-butyl group, a fluorine atom, a chlorine atom, a bromine atom or an iodine atom on the ortho-, meta- or para-position of the benzene ring), a substituted phenyl group (which is substituted with a methyl group, an ethyl group, an n-propyl group, an i-propyl group, an n-butyl group, an i-butyl group, a sec-butyl group, a t-butyl group, a fluorine atom, a chlorine atom, a bromine atom, an iodine atom, a formylamino group, an acetylamino group, a propionylamino group, a butyrylamino group, a methylsulfonylamino group, an ethylsulfonylamino group, an N-n-propylsulfonylamino group, an N-i-propylsulfonylamino group, an N-n-butylsulfonylamino group, an N-i-butylsulfonylamino group, an N-sec-butylsulfonylamino group, an N-t-butylsulfonylamino group, an N-phenylsulfonylamino group, a hydroxy group, a methoxy group, an ethoxy group, an n-propoxy group, an i-propoxy group, an n-butoxy group, an i-butoxy group, a sec-butoxy group, a t-butoxy group, an N-substituted phenylsulfonylamino group (which is substituted with a methyl group, an ethyl group, an n-propyl group, an i-propyl group, an n-butyl group, an i-butyl group, a sec-butyl group, a t-butyl group, a fluorine atom, a chlorine atom, a bromine atom or an iodine atom on the ortho-, meta- or para-position of the benzene ring), a methylthio group, an ethylthio group, an n-propylthio group, an i-propylthio group, an n-butylthio group, an i-butylthio group, a sec-butylthio group, a t-butylthio group, a methylsulfoxy group, an ethylsulfoxy group, an n-propylsulfoxy group, an i-propylsulfoxy group, an n-butylsulfoxy group, an i-butylsulfoxy group, a sec-butylsulfoxy group, a t-butylsulfoxy group, a methylsulfonyl group, an ethylsulfonyl group, an n-propylsulfonyl group, an i-propylsulfonyl group, an n-butylsulfonyl group, an i-butylsulfonyl group, a sec-butylsulfonyl group, or a t-butylsulfonyl group on the ortho-, meta- or para-position of the benzene ring), an N-phenylcarbonylamino group, a 1-(2-oxo)azetidinyl group, a 1-(2-oxo)pyrrolidinyl group, a 1-(2-oxo)piperidinyl group, a 1-(2-oxo)homopiperidinyl group, a 1-(2-oxo-3,3-dimethyl)pyrrolidinyl group, a 1-(2-oxo-5,5-dimethyl)pyrrolidinyl group, an N-methoxycarbonylamino group, an N-ethoxycarbonylamino group, an N-n-propoxycarbonylamino group, an N-i-propoxycarbonylamino group, an N-n-butoxycarbonylamino group, an N-i-butoxycarbonylamino group, an N-sec-butoxycarbonylamino group, an N-t-butoxycarbonylamino group, a 3-(2-oxo)oxazolidinyl group, a 3-(2-oxo-5,5-dimethyl)oxazolidinyl group, a 3-(2-oxo-4,4-diethyl)oxazolidinyl group, a 3-(2-oxo-5,5-diethyl)oxazolidinyl group, an N,N-di-substituted amino group (having an optional combination of a methyl group, an ethyl group, an n-propyl group, an i-propyl group, an n-butyl group, an i-butyl group, a sec-butyl group and a t-butyl group), a 1-azetidino group, a 1-pyrrolidino group, a 1-piperidino group, a 1-(2,5-dimethyl)pyrrolidino group, a 1-(3,4-dimethyl)pyrrolidino group, a 1-(4,4-dimethyl)piperidino group, a 1-(4-phenylmethyl)piperadino group, 1-(4-diphenylmethyl)piperadino group, a 1-(4-substituted phenylmethyl)piperadinyl or 1-(4-di-substituted phenylmethyl)piperadinyl group (which is substituted with a fluorine atom, a chlorine atom, a bromine atom or an iodine atom on the ortho-, meta- or para-position of the benzene ring), a phenylaminocarboxyl group, an N,N-di-substituted aminocarbonyl group (having an optional combination of a linear or cyclic alkyl group, a phenyl group, a thiazolyl group or a thiadiazolyl group on the above described N-substituted aminocarbonyl groups), N-alkyl-N-phenylsulfonylamino, N,N-dialkylsulfonylamino or N-alkyl-N-alkoxycarbonylamino groups (having a linear or branched $C_1$–$C_4$ alkyl substituent on the nitrogen atom of the above described N-phenylsulfonylamino, N-alkylsulfonylamino or N-alkoxycarbonylamino groups), di-substituted phenyl groups (which are substituted on the ortho-, meta- or para-position of the benzene ring with an optional combination of a halogen atom, a linear alkyl group, an acylamino group, a hydroxy group, an alkoxy group, an N-phenylsulfonylamino group, an N-alkylsulfonylamino group, a linear alkylthio group and a linear alkylsulfonyl group on the above described substituted phenyl groups), and the like.

Examples of $Y^2$ include a phenyl group.

Examples of $R^3$ and $R^4$ include a hydrogen atom, a methyl group, an ethyl group, an n-propyl group and an i-propyl group, preferably a hydrogen atom.

Examples of X include a hydrogen atom, a chlorine atom, a bromine atom and a cyano group, preferably each substituent other than a hydrogen atom.

Examples of Ar include a 2-pyridyl group, a 3-pyridyl group, a 4-pyridyl group, a substituted 2-pyridyl group, 3-pyridyl or 4-pyridyl (which is substituted with a fluorine atom, a chlorine atom, a bromine atom and an iodine atom, a methoxy group, an ethoxy group, an n-propoxy group, an i-propoxy group, an n-butoxy group, an i-butoxy group, a sec-butoxy group or a t-butoxy group on the 2-, 3-, 4-, 5- or 6-position of the pyridine ring), an N-oxidopyrizyl group corresponding to the above described pyridyl or substituted pyridyl group, a 2-furyl group, a 3-furyl group, a 2-thienyl group, a 3-thienyl group, a 1-naphthyl group, a 2-naphthyl group, a 1-naphthyl or 2-naphthyl group (which is substituted with a hydroxy group, a methoxy group, an ethoxy group, an n-propoxy group, an i-propoxy group, an n-butoxy group, an i-butoxy group, a sec-butoxy group or a t-butoxy group on an optional position of the naphthalene ring) or substituted phenyl groups having the following one or two substituents in optional combination at an optional position. Examples of the substituents include a hydrogen atom, a fluorine atom, a chlorine atom, a bromine atom, an iodine atom, a methyl group, an ethyl group, an n-propyl group, an i-propyl group, an n-butyl group, an i-butyl group, a sec-butyl group, a t-butyl group, a hydroxy group, an alkoxy group (having a linear or branched $C_1$–$C_8$ alkyl group), a dioxyemthylene, 1,2-dioxyethylene or 1,3-dioxypropylene group (which comprises adjacent two substituents joined together), or an O—$A^1$—$Y^3$ group. $A^1$ is a linear or branched $C_1$–$C_{10}$ alkylene group, $Y^3$ is a phenyl group, a substituted phenyl group (which is substituted with a methyl group, an ethyl group, an n-propyl group, an i-propyl group, an n-butyl group, an i-butyl group, a sec-butyl group, a t-butyl group, a fluorine atom, a chlorine atom, a bromine atom or an iodine atom on the ortho-, meta- or para-position of the benzene ring), or the above-mentioned (with regard to $Y^1$) carboxyl, alkoxycarbonyl, 1-cycloaminocarbonyl, 1-morpholinocarbonyl, or carbamoyl, N-substituted or N,N-disubstituted aminocarbonyl group (having on a nitrogen atom an optional combination of two substituents of a hydrogen atom, a linear, branched or cyclic alkyl group, a phenyl group, a thiazolyl group and a thiadiazolyl group). Preferable examples include a 3-pyridyl group or 3-substituted-4-methoxyphenyl type group, but the present invention should not be limited to these examples.

In the above description "n", "i", "sec" and "t" respectively stand for "normal", "iso", "secondary" and "tertiary".

Preferably compounds of the compounds having the general formula [I] of the present invention are represented by the following general formula [IC],

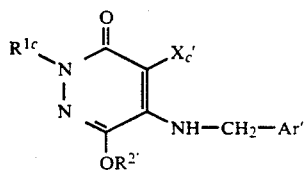
[IC]

{wherein $R^{1c}$ is a hydrogen atom;
  $R^{2'}$ is $A^1$-$Y^{3'}$ [$A^1$ is a straight chained or branched $C_1$-$C_{12}$ alkylene group, $Y^{3'}$ is $CO_2R^{5'}$ ($R^{5'}$ is a straight chained or branched $C_{1-4}$ alkyl group),

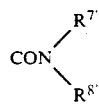

($R^{7'}$ and $R^{8'}$ are respectively and independently a hydrogen atom, a straight chained or branched $C_1$-$C_4$ alkyl group, a $C_3$-$C_8$ cycloalkyl group or a phenyl group, $R^{7'}$ and $R^{8'}$ together form a $C_2$-$C_8$ alkylene group which may be substituted with a straight chained $C_1$-$C_3$ alkyl group or a phenyl group, or form a morpholine ring with a nitrogen atom),

($R^5$ is a hydrogen atom or a straight chained or branched $C_1$-$C_4$ alkyl group, $R^{9'}$ is a phenyl group which may be substituted with a straight chained or branched $C_1$-$C_4$ alkyl group or a halogen atom),

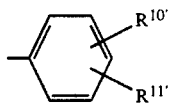

($R^{10'}$ and $R^{11'}$ are respectively and independently a hydrogen atom, a halogen atom, a straight chained or branched $C_1$-$C_4$ alkyl group, A $C_1$-$C_4$ acylamino group, $OR^5$ ($R^5$ is as defined above), $NHSO_2R^{9''}$ ($R^{9''}$ is a straight chained or branched $C_1$-$C_4$ alkyl group) or $S(O)_m$-$R^{12}$ (m is 0 or 2 and $R^{12}$ is a straight chained or branched $C_1$-$C_4$ alkyl group), provided that $R^{10'}$ and $R^{11'}$ are not hydrogen atoms at the same time),

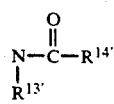

($R^{13'}$ is a hydrogen atom, $R^{14'}$ is a phenyl group, or $R^{13'}$ and $R^{14'}$ together form a $C_2$-$C_5$ alkylene group),

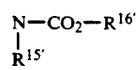

($R^{15'}$ is a hydrogen atom or a straight chained or branched $C_1$-$C_4$ alkyl group, $R^{16'}$ is a straight chained or branched $C_1$-$C_4$ alkyl group, or $R^{15'}$ and $R^{16'}$ together form a $C_2$-$C_6$ alkylene group,

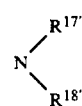

($R^{17'}$ and $R^{18'}$ are respectively and independently a straight chained or branched $C_1$-$C_4$ alkyl group, or $R^{17'}$ and $R^{18'}$ together form a $C_2$-$C_6$ alkylene group),

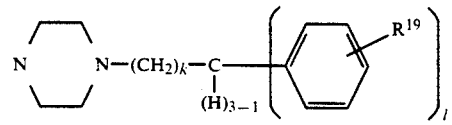

(l is 1 or 2, and $R^{19}$ is a hydrogen atom or a halogen atom), or

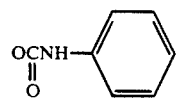

]; or $R^2$ is $A^2$-$Y^2$ ($A^2$ is a $C_2$-$C_8$ alkylene group which may be substituted with a straight chained $C_1$-$C_3$ alkyl group, except for the case that a carbon chain connecting an oxygen atom with $Y^2$ has one carbon, and $Y^2$ is a phenyl group);
  $X_c'$ is a chlorine atom, a bromine atom, or a cyano group; and
  $Ar'$ is a 3-pyridyl group, or

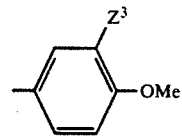

[$Z^3$ is a halogen atom, a straight chained or branched $C_1$-$C_4$ alkyl group, $OR^{22}$ ($R^{22}$ is a hydrogen atom or a straight chained or branched $C_{1-8}$ alkyl group) or O—$A^3$—$Y^3$ ($A^3$ is a $C_1$-$C_4$ alkylene group, $Y^3$ is a phenyl group, $CO_2R^{5'}$,

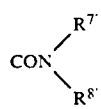

(R⁵', R⁷' and R⁸' are as defined above))]}.

The compounds of the general formula [I] of the present invention include optical isomers and stereoisomers based on from 1 to 6 asymmetric carbon atoms.

Hereinafter, typical compounds of the 3(2H)-pyridazinone derivatives of the general formula [I] and pharmaceutically acceptable salts thereof of the present invention are illustrated in the following Table 1, but the present invention should not be limited thereto.

In Table 1, "n" stands for normal, "i" stands for iso, "sec" stands for secondary, "Me" stands for a methyl group, "Et" stands for an ethyl group, "Pr" stands for a propyl group, "Bu" stands for a butyl group, "Pen" stands for a pentyl group, "Hex" stands for a hexyl group, "Hep" stands for a heptyl group, "Oct" stands for an octyl group, "Ac" stands for an acetyl group, and "Ph" stands for a phenyl group.

Q1–Q108 in Table I are groups represented by the following formulas.

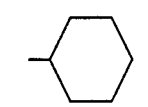 Q1

 Q2

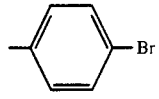 Q3

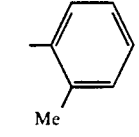 Q4

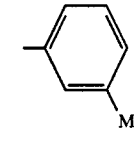 Q5

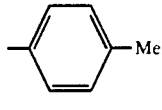 Q6

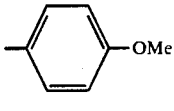 Q7

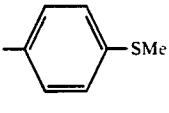 Q8

-continued

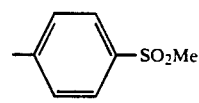 Q9

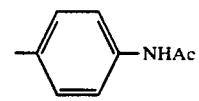 Q10

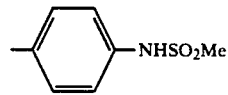 Q11

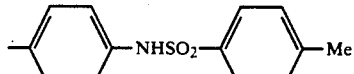 Q12

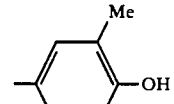 Q13

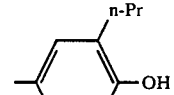 Q14

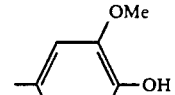 Q15

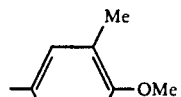 Q16

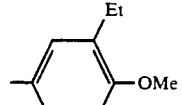 Q17

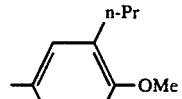 Q18

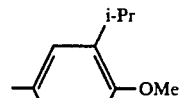 Q19

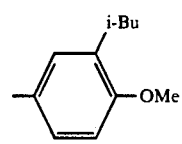 Q20

-continued
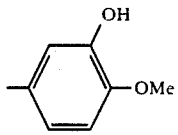 Q21
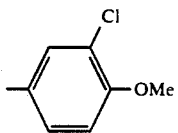 Q22
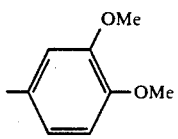 Q23
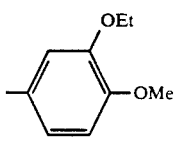 Q24
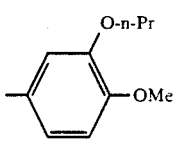 Q25
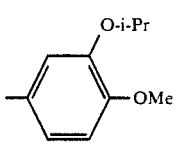 Q26
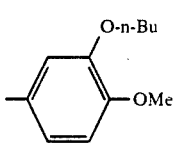 Q27
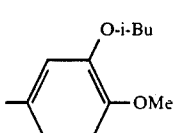 Q28
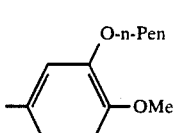 Q29
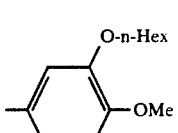 Q30
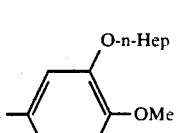 Q31
-continued
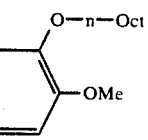 Q32
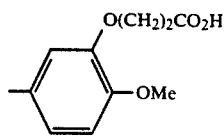 Q33
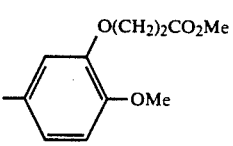 Q34
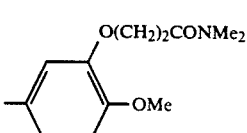 Q35
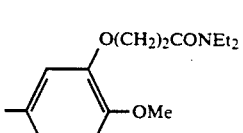 Q36
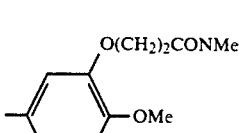 Q37
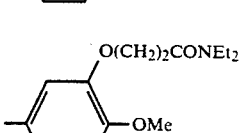 Q38
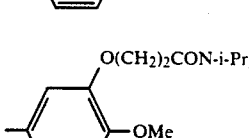 Q39
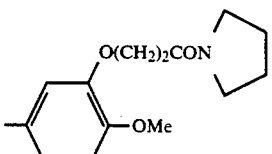 Q40
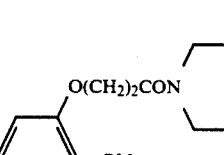 Q41

-continued
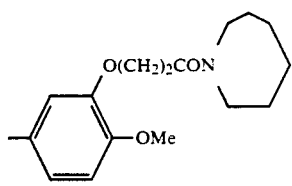 Q42
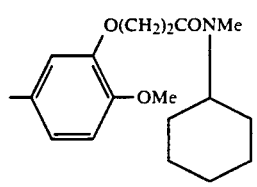 Q43
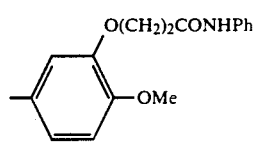 Q44
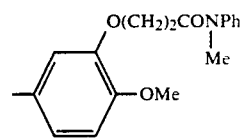 Q45
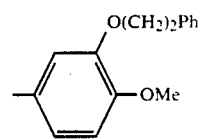 Q46
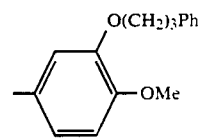 Q47
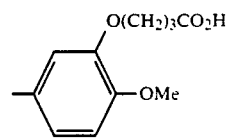 Q48
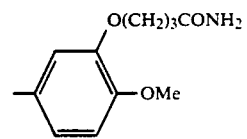 Q49
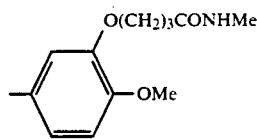 Q50
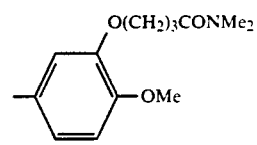 Q51
-continued
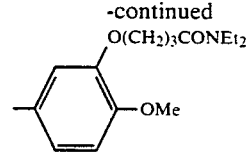 Q52
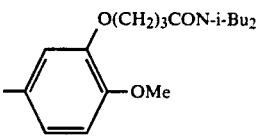 Q53
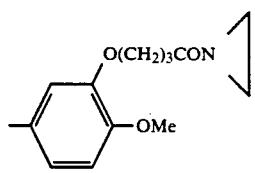 Q54
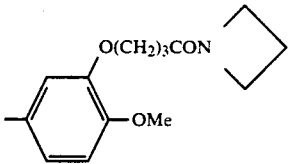 Q55
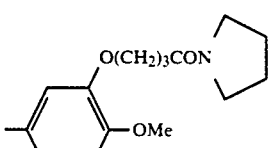 Q56
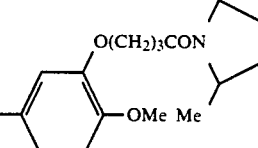 Q57
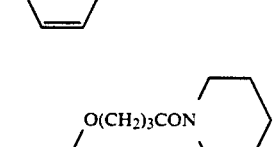 Q58
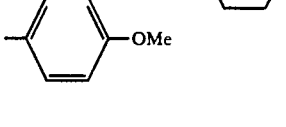 Q59
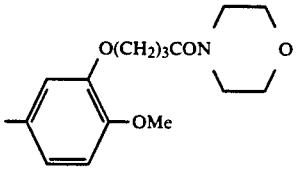 Q59
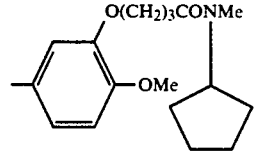 Q60

-continued
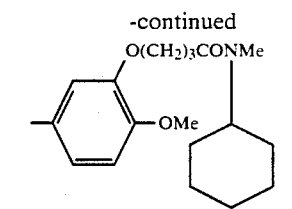 Q61
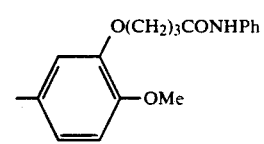 Q62
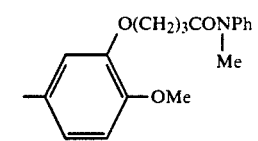 Q63
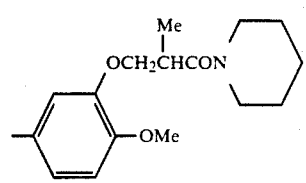 Q64
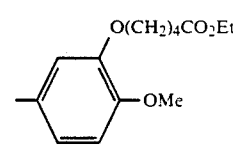 Q65
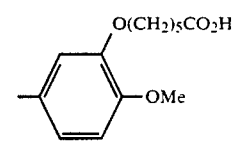 Q66
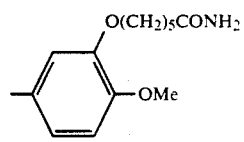 Q67
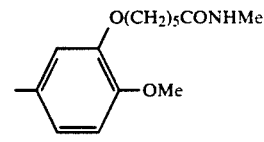 Q68
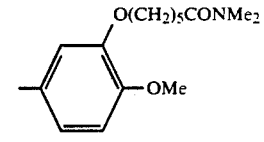 Q69
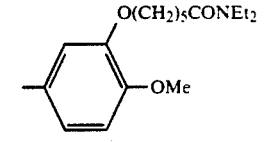 Q70
-continued
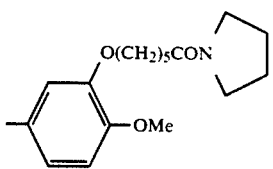 Q71
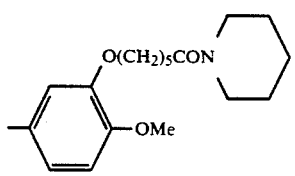 Q72
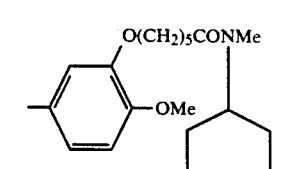 Q73
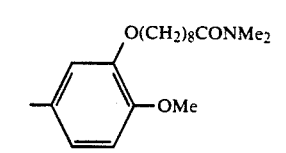 Q74
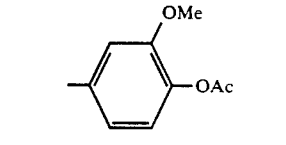 Q75
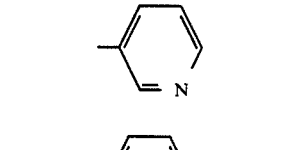 Q76
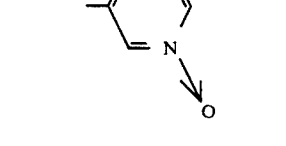 Q77
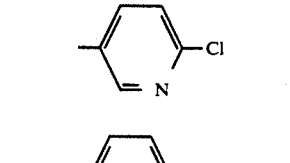 Q78
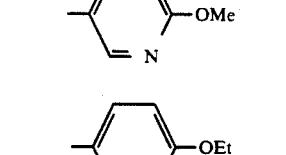 Q79
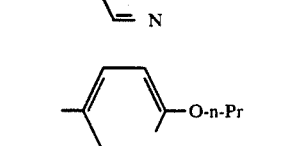 Q80
Q81

-continued
| | | | |
|---|---|---|---|
|  | Q82 |  | Q94 |
| 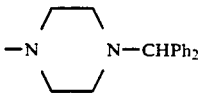 | Q83 | 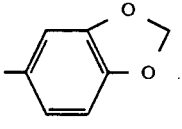 | Q95 |
|  | Q84 |  | Q96 |
| 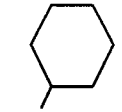 | Q85 | 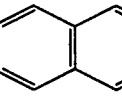 | Q97 |
|  | Q86 |  | Q98 |
| 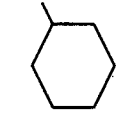 | Q87 | 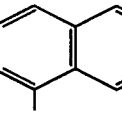 | Q99 |
| 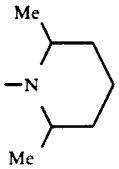 | Q88 |  | Q100 |
| 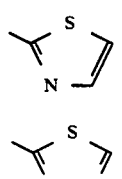 | Q89 | 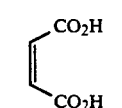 | Q101 |
| 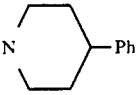 | Q90 |  | Q102 |
| 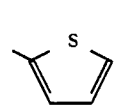 | Q91 | 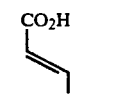 | Q103 |
|  | Q92 |  | Q104 |
| 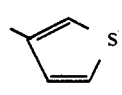 | Q93 | 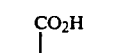 | Q105 |
| | |  | Q106 |

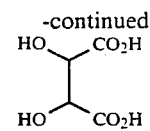

Q107

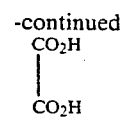

Q108

TABLE I

| No. | R¹ | R² | R³ | R⁴ | X | Ar |
|---|---|---|---|---|---|---|
| 1 | H | $(CH_2)_5CO_2Me$ | H | H | Cl | Q23 |
| 2 | H | $(CH_2)_5CO_2H$ | H | H | Cl | Q23 |
| 3 | H | $(CH_2)_5CO_2Me$ | H | H | Cl | Q76 |
| 4 | H | $(CH_2)_5CO_2H$ | H | H | Cl | Q76 |
| 5 | H | $CH_2CO_2Et$ | H | H | Cl | Q76 |
| 6 | H | $CH_2CO_2H$ | H | H | Cl | Q76 |
| 7 | H | $CH_2CO_2Me$ | H | H | Cl | Q76.HCl |
| 8 | H | $(CH_2)_5CONHMe$ | H | H | Cl | Q23 |
| 9 | H | $(CH_2)_5CONMe_2$ | H | H | Cl | Q23 |
| 10 | H | $(CH_2)_5CONH_2$ | H | H | Cl | Q23 |
| 11 | H | $(CH_2)_5CO-Q87$ | H | H | Cl | Q23 |
| 12 | H | $(CH_2)_5CONEt_2$ | H | H | Cl | Q23 |
| 13 | H | $(CH_2)_5CON(Me)-Q1$ | H | H | Cl | Q23 |
| 14 | H | $(CH_2)_3CO_2Et$ | H | H | Cl | Q23 |
| 15 | H | $(CH_2)_3CO_2H$ | H | H | Cl | Q23 |
| 16 | H | $(CH_2)_3CONMe_2$ | H | H | Cl | Q23 |
| 17 | H | $(CH_2)_3CONEt_2$ | H | H | Cl | Q23 |
| 18 | H | $(CH_2)_3CO-Q87$ | H | H | Cl | Q23 |
| 19 | H | $CH_2CO_2Et$ | H | H | Cl | Q23 |
| 20 | H | $CH_2CO_2H$ | H | H | Cl | Q23 |
| 21 | H | $(CH_2)_3NHSO_2-Q2$ | H | H | Cl | Q23 |
| 22 | H | $(CH_2)_3NHSO_2-Q2$ | H | H | Cl | Q76 |
| 23 | H | $(CH_2)_2NHSO_2Ph$ | H | H | Cl | Q23 |
| 24 | H | $(CH_2)_2NHSO_2Ph$ | H | H | Cl | Q76 |
| 25 | H | $(CH_2)_5CON-n-Pr_2$ | H | H | Cl | Q23 |
| 26 | H | $(CH_2)_5CO-Q83$ | H | H | Cl | Q23 |
| 27 | H | $(CH_2)_5CO-Q82$ | H | H | Cl | Q23 |
| 28 | H | $(CH_2)_5CONEt_2$ | H | H | Cl | Q76 |
| 29 | H | $(CH_2)_5CONMe_2$ | H | H | Cl | Q76 |
| 30 | H | $(CH_2)_7CO_2Me$ | H | H | Cl | Q23 |
| 31 | H | $(CH_2)_7CO_2H$ | H | H | Cl | Q23 |
| 32 | H | $(CH_2)_5CO-Q82$ | H | H | Cl | Q76 |
| 33 | H | $(CH_2)_5CO-Q83$ | H | H | Cl | Q76 |
| 34 | H | $(CH_2)_7CONMe_2$ | H | H | Cl | Q23 |
| 35 | H | $(CH_2)_7CONEt_2$ | H | H | Cl | Q23 |
| 36 | H | $(CH_2)_7CON-n-Pr_2$ | H | H | Cl | Q23 |
| 37 | H | $(CH_2)_7CO-Q82$ | H | H | Cl | Q23 |
| 38 | H | $(CH_2)_7CO-Q83$ | H | H | Cl | Q23 |
| 39 | H | $(CH_2)_7CO-Q87$ | H | H | Cl | Q23 |
| 40 | H | $(CH_2)_5CO_2Me$ | H | H | Cl | Q16 |
| 41 | H | $(CH_2)_5CO_2Me$ | H | H | Br | Q23 |
| 42 | H | $(CH_2)_5CO_2H$ | H | H | Br | Q23 |
| 43 | H | $(CH_2)_5CONMe_2$ | H | H | Br | Q23 |
| 44 | H | $(CH_2)_5$-Q82 | H | H | Br | Q23 |
| 45 | H | $(CH_2)_5$-Q83 | H | H | Br | Q23 |
| 46 | H | $(CH_2)_5CONEt_2$ | H | H | Br | Q23 |
| 47 | H | $(CH_2)_5CON-n-Pr_2$ | H | H | Br | Q23 |
| 48 | H | $(CH_2)_5CO-Q87$ | H | H | Br | Q23 |
| 49 | H | $(CH_2)_5CO_2H$ | H | H | Cl | Q16 |
| 50 | H | $(CH_2)_3CO-Q83$ | H | H | Cl | Q23 |
| 51 | H | $(CH_2)_5CO-Q83$ | H | H | Cl | Q76 |
| 52 | H | $(CH_2)_7CO-Q83$ | H | H | Cl | Q76.HCl |
| 53 | H | $(CH_2)_5CONMe_2$ | H | H | Cl | Q16 |
| 54 | H | $(CH_2)_5CONEt_2$ | H | H | Cl | Q16 |
| 55 | H | $(CH_2)_5CON-n-Pr_2$ | H | H | Cl | Q16 |
| 56 | H | $(CH_2)_5CO-Q82$ | H | H | Cl | Q16 |
| 57 | H | $(CH_2)_5CO-Q83$ | H | H | Cl | Q16 |
| 58 | H | $(CH_2)_5CO-Q87$ | H | H | Cl | Q16 |
| 59 | H | $(CH_2)_7CO_2Me$ | H | H | Br | Q23 |
| 60 | H | $(CH_2)_3CO-Q84$ | H | H | Cl | Q23 |
| 61 | H | $(CH_2)_5CO-Q84$ | H | H | Cl | Q23 |
| 62 | H | $(CH_2)_7CO-Q84$ | H | H | Cl | Q23 |
| 63 | H | $(CH_2)_7CONMe_2$ | H | H | Br | Q23 |
| 64 | H | $(CH_2)_7CONEt_2$ | H | H | Br | Q23 |

TABLE I-continued

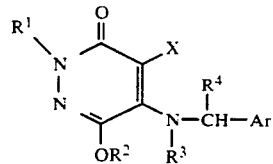

| No. | $R^1$ | $R^2$ | $R^3$ | $R^4$ | X | Ar |
|---|---|---|---|---|---|---|
| 65 | H | $(CH_2)_7CON$-n-$Pr_2$ | H | H | Br | Q23 |
| 66 | H | $(CH_2)_7CO$-Q82 | H | H | Br | Q23 |
| 67 | H | $(CH_2)_7CO$-Q83 | H | H | Br | Q23 |
| 68 | H | $(CH_2)_7CO$-Q87 | H | H | Br | Q23 |
| 69 | H | $(CH_2)_4CO$-Q83 | H | H | Cl | Q76 |
| 70 | H | $(CH_2)_4CO$-Q83 | H | H | Br | Q76 |
| 71 | H | $(CH_2)_4CO$-Q83 | H | H | Cl | Q23 |
| 72 | H | $(CH_2)_5CO$-Q83 | H | H | Cl | Q76.HCl |
| 73 | H | $(CH_2)_5CO$-Q83 | H | H | Cl | Q76.Q105 |
| 74 | H | $(CH_2)_5CO$-Q85 | H | H | Cl | Q76 |
| 75 | H | $(CH_2)_5CO$-Q85 | H | H | Cl | Q76.HCl |
| 76 | H | $(CH_2)_5CO$-Q85 | H | H | Cl | Q76.Q105 |
| 77 | H | $(CH_2)_3CO$-Q85 | H | H | Cl | Q76 |
| 78 | H | $(CH_2)_3CO$-Q83 | H | H | Cl | Q76.HCl |
| 79 | H | $(CH_2)_3CO$-Q85 | H | H | Cl | Q76.HCl |
| 80 | H | $(CH_2)_2Ph$ | H | H | Br | Q76.HCl |
| 81 | H | $(CH_2)_4CO$-Q83 | H | H | Cl | Q76.HCl |
| 82 | H | $(CH_2)_4CO$-Q83 | H | H | Br | Q76.HCl |
| 83 | H | $(CH_2)_2Ph$ | H | H | Br | Q23 |
| 84 | H | $(CH_2)_3Ph$ | H | H | Br | Q23 |
| 85 | H | $(CH_2)_3Ph$ | H | H | Br | Q76.HCl |
| 86 | H | $(CH_2)_5CO$-Q95 | H | H | Cl | Q23 |
| 87 | H | $(CH_2)_7CO$-Q95 | H | H | Cl | Q23 |
| 88 | H | $(CH_2)_3Ph$ | H | H | Br | Q58 |
| 89 | H | $(CH_2)_5CO_2H$ | H | H | Br | Q76 |
| 90 | H | $(CH_2)_3Ph$ | H | H | Cl | Q23 |
| 91 | H | $(CH_2)_3Ph$ | H | H | Cl | Q76 |
| 92 | H | $(CH_2)_3Ph$ | H | H | Cl | Q76.HCl |
| 93 | H | $(CH_2)_3Ph$ | H | H | Cl | Q76.Q105 |
| 94 | H | $(CH_2)_3Ph$ | H | H | Br | Q61 |
| 95 | H | $(CH_2)_4NHSO_2Ph$ | H | H | Cl | Q76 |
| 96 | H | $(CH_2)_4NHSO_2Ph$ | H | H | Br | Q23 |
| 97 | H | $(CH_2)_4NHSO_2Ph$ | H | H | Br | Q76 |
| 98 | H | $(CH_2)_6NHSO_2Ph$ | H | H | Br | Q23 |
| 99 | H | $(CH_2)_6NHSO_2Ph$ | H | H | Br | Q76 |
| 100 | H | $(CH_2)_4NHSO_2Ph$ | H | H | Cl | Q23 |
| 101 | H | $(CH_2)_3Ph$ | H | H | Br | Q76 |
| 102 | H | $(CH_2)_4Ph$ | H | H | Br | Q76 |
| 103 | H | $(CH_2)_4Ph$ | H | H | Br | Q23 |
| 104 | H | $(CH_2)_3$-Q10 | H | H | Br | Q76 |
| 105 | H | $(CH_2)_3$-Q2 | H | H | Cl | Q76 |
| 106 | H | $(CH_2)_3$-Q2 | H | H | Br | Q76 |
| 107 | H | $(CH_2)_3$-Q2 | H | H | CN | Q76 |
| 108 | H | $(CH_2)_3$-Q88 | H | H | Br | Q76 |
| 109 | H | $(CH_2)_3$-Q88 | H | H | Br | Q23 |
| 110 | H | $(CH_2)_3$-Q88 | H | H | Br | Q28 |
| 111 | H | $(CH_2)_3$-Q90 | H | H | Br | Q76 |
| 112 | H | $(CH_2)_3$-Q90 | H | H | Br | Q23 |
| 113 | H | $(CH_2)_5CONHPh$ | H | H | Br | Q76.HCl |
| 114 | H | $(CH_2)_3CONHPh$ | H | H | Br | Q76 |
| 115 | H | $(CH_2)_3CONH$-Q96 | H | H | Br | Q23 |
| 116 | H | $(CH_2)_3CONH$-Q97 | H | H | Br | Q23 |
| 117 | H | $(CH_2)_5CONH$-Q97 | H | H | Br | Q23 |
| 118 | H | $(CH_2)_3CONEt_2$ | H | H | Br | Q76 |
| 119 | H | $(CH_2)_5CON(Me)$-Q1 | H | H | Br | Q76 |
| 120 | H | $(CH_2)_5CON(Me)$-Q1 | H | H | Br | Q23 |
| 121 | H | $(CH_2)_5CON(Me)-Ph$ | H | H | Br | Q76.HCl |
| 122 | H | $(CH_2)_3CON(Me)-Ph$ | H | H | Br | Q76 |
| 123 | H | $(CH_2)_5CON(Et)-Ph$ | H | H | Br | Q76.HCl |
| 124 | H | $(CH_2)_3CON(Et)-Ph$ | H | H | Br | Q76 |
| 125 | H | $(CH_2)_5CON(Et)-Ph$ | H | H | Br | Q23 |
| 126 | H | $(CH_2)_5CO$-Q87 | H | H | Br | Q76.HCl |
| 127 | H | $(CH_2)_3CO$-Q87 | H | H | Br | Q76 |
| 128 | H | $(CH_2)_5CO$-Q86 | H | H | Cl | Q23 |
| 129 | H | $(CH_2)_4NHCOPh$ | H | H | Br | Q76 |
| 130 | H | $(CH_2)_4NHCOPh$ | H | H | Br | Q23 |
| 131 | H | $(CH_2)_6$-Q88 | H | H | Br | Q76 |
| 132 | H | $(CH_2)_5$-Q88 | H | H | Br | Q76 |
| 133 | H | $(CH_2)_6$-Q88 | H | H | Br | Q23 |
| 134 | H | $(CH_2)_6$-Q90 | H | H | Br | Q76 |
| 135 | H | $(CH_2)_5$-Q90 | H | H | Br | Q76.HCl |
| 136 | H | $(CH_2)_5NHSO_2Me$ | H | H | Br | Q76 |

TABLE I-continued

| No. | R¹ | R² | R³ | R⁴ | X | Ar |
|---|---|---|---|---|---|---|
| 137 | H | (CH$_2$)$_5$-Q90 | H | H | Br | Q23 |
| 138 | H | (CH$_2$)$_3$NHSO$_2$Me | H | H | Br | Q76 |
| 139 | H | (CH$_2$)$_5$NHSO$_2$Me | H | H | Br | Q23 |
| 140 | H | (CH$_2$)$_3$NHSO$_2$Me | H | H | Br | Q23 |
| 141 | H | (CH$_2$)$_2$N(Me)SO$_2$Ph | H | H | Br | Q76 |
| 142 | H | (CH$_2$)$_4$N(Me)SO$_2$Ph | H | H | Br | Q76 |
| 143 | H | (CH$_2$)$_4$N(Me)SO$_2$Ph | H | H | Br | Q23 |
| 144 | H | (CH$_2$)$_4$N(Me)SO$_2$Ph | H | H | Br | Q23 |
| 145 | H | (CH$_2$)$_3$N(Me)SO$_2$Me | H | H | Br | Q76 |
| 146 | H | (CH$_2$)$_5$N(Me)SO$_2$Me | H | H | Br | Q76 |
| 147 | H | (CH$_2$)$_3$N(Me)SO$_2$Me | H | H | Br | Q23 |
| 148 | H | (CH$_2$)$_5$N(Me)SO$_2$Me | H | H | Br | Q23 |
| 149 | H | (CH$_2$)$_4$NHCO$_2$Me | H | H | Br | Q76 |
| 150 | H | (CH$_2$)$_5$NHCO$_2$Me | H | H | Br | Q76 |
| 151 | H | (CH$_2$)$_3$NHCO$_2$Me | H | H | Br | Q76 |
| 152 | H | (CH$_2$)$_4$NHCO$_2$Me | H | H | Br | Q23 |
| 153 | H | (CH$_2$)$_5$NHCO$_2$Me | H | H | Br | Q23 |
| 154 | H | (CH$_2$)$_4$N(Me)CO$_2$Me | H | H | Br | Q76 |
| 155 | H | (CH$_2$)$_5$N(Me)CO$_2$Me | H | H | Br | Q76 |
| 156 | H | (CH$_2$)$_3$N(Me)CO$_2$Me | H | H | Br | Q76 |
| 157 | H | (CH$_2$)$_4$N(Me)CO$_2$Me | H | H | Br | Q23 |
| 158 | H | (CH$_2$)$_5$N(Me)CO$_2$Me | H | H | Br | Q23 |
| 159 | H | (CH$_2$)$_5$-Q89 | H | H | Br | Q76 |
| 160 | H | (CH$_2$)$_6$-Q89 | H | H | Br | Q76 |
| 161 | H | (CH$_2$)$_4$-Q89 | H | H | Br | Q76 |
| 162 | H | (CH$_2$)$_6$-Q89 | H | H | Br | Q23 |
| 163 | H | (CH$_2$)$_4$-Q89 | H | H | Br | Q23 |
| 164 | H | (CH$_2$)$_4$OCONHPh | H | H | Br | Q76.HCl |
| 165 | H | (CH$_2$)$_6$OCONHPh | H | H | Br | Q76.HCl |
| 166 | H | (CH$_2$)$_3$-Q2 | H | H | Br | Q76.HCl |
| 167 | H | (CH$_2$)$_3$-Q2 | H | H | Cl | Q76.HCl |
| 168 | H | (CH$_2$)$_4$-Q2 | H | H | Cl | Q76 |
| 169 | H | (CH$_2$)$_3$-Q2 | H | H | Br | Q76.Q104 |
| 170 | H | (CH$_2$)$_3$-Q2 | H | H | Br | Q76.Q107 |
| 171 | H | (CH$_2$)$_3$-Q2 | H | H | Br | Q76.Q106 |
| 172 | H | (CH$_2$)$_3$-Q2 | H | H | Br | Q76.Q108 |
| 173 | H | (CH$_2$)$_3$-Q7 | H | H | Br | Q76 |
| 174 | H | (CH$_2$)$_4$-Q7 | H | H | Br | Q76 |
| 175 | H | (CH$_2$)$_5$-Q7 | H | H | Br | Q76 |
| 176 | H | (CH$_2$)$_5$-Q7 | H | H | Cl | Q76 |
| 177 | H | (CH$_2$)$_3$-Q7 | H | H | Br | Q23 |
| 178 | H | (CH$_2$)$_3$-Q11 | H | H | Br | Q23 |
| 179 | H | (CH$_2$)$_3$-Q12 | H | H | Br | Q76 |
| 180 | H | (CH$_2$)$_3$-Q8 | H | H | Br | Q76 |
| 181 | H | (CH$_2$)$_2$C(Me$_2$)-Q2 | H | H | Br | Q76.HCl |
| 182 | H | (CH$_2$)$_3$-Q23 | H | H | Br | Q76 |
| 183 | H | (CH$_2$)$_3$-Q23 | H | H | Br | Q23 |
| 184 | H | (CH$_2$)$_3$-Q25 | H | H | Br | Q76 |
| 185 | H | (CH$_2$)$_3$-Q25 | H | H | Br | Q23 |
| 186 | H | (CH$_2$)$_3$-Q26 | H | H | Br | Q76 |
| 187 | H | (CH$_2$)$_3$-Q26 | H | H | Br | Q23 |
| 188 | H | (CH$_2$)$_3$-Q15 | H | H | Br | Q76 |
| 189 | H | (CH$_2$)$_3$-Q15 | H | H | Br | Q23 |
| 190 | H | (CH$_2$)$_3$-Q13 | H | H | Br | Q76 |
| 191 | H | (CH$_2$)$_3$-Q14 | H | H | Br | Q76 |
| 192 | H | (CH$_2$)$_3$-Q75 | H | H | Br | Q23 |
| 193 | H | (CH$_2$)$_3$-Q98 | H | H | Br | Q76.HCl |
| 194 | H | (CH$_2$)$_3$-Q99 | H | H | Br | Q76 |
| 195 | H | (CH$_2$)$_3$-Q99 | H | H | Br | Q23 |
| 196 | H | (CH$_2$)$_3$-Q76 | H | H | Br | Q76 |
| 197 | H | (CH$_2$)$_3$-Q76 | H | H | Br | Q23 |
| 198 | H | (CH$_2$)$_2$OPh | H | H | Br | Q76 |
| 199 | H | (CH$_2$)$_2$OPh | H | H | Br | Q23 |
| 200 | H | (CH$_2$)$_6$CN | H | H | Br | Q76 |
| 201 | H | (CH$_2$)$_6$CN | H | H | Br | Q23 |
| 202 | H | (CH$_2$)$_2$-Q82.HCl | H | H | Br | Q23 |
| 203 | H | (CH$_2$)$_3$NMe$_2$.HCl | H | H | Br | Q23 |
| 204 | H | (CH$_2$)$_2$NEt$_2$.HCl | H | H | Br | Q23 |
| 205 | H | (CH$_2$)$_3$-Q92.2HCl | H | H | Br | Q23 |
| 206 | H | (CH$_2$)$_3$-Q93.2HCl | H | H | Br | Q23 |
| 207 | H | (CH$_2$)$_3$-Q94.2HCl | H | H | Br | Q23 |
| 208 | H | (CH$_2$)$_3$Ph | H | H | Cl | Q101 |

TABLE I-continued

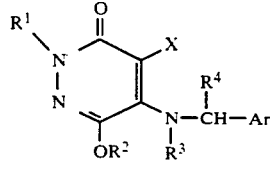

| No. | R¹ | R² | R³ | R⁴ | X | Ar |
|---|---|---|---|---|---|---|
| 209 | H | $(CH_2)_5CONEt_2$ | H | H | Cl | Q101 |
| 210 | H | $C(Me)H(CH_2)_2Ph$ | H | H | Br | Q76.HCl |
| 211 | H | $(CH_2)_3Ph$ | Me | H | Cl | Q101 |
| 212 | H | $(CH_2)_2C(Me_2)$-Q2 | H | H | Br | Q101 |
| 213 | H | $(CH_2)_3$-Q93.2HCl | H | H | Br | Q101 |
| 214 | H | $CH_2C(Me)_2CH_2$-Q2 | H | H | Cl | Q76 |
| 215 | H | $C(Me)H(CH_2)_2Ph$ | H | H | Br | Q101 |
| 216 | H | $(CH_2)_3$-Q2 | H | H | Cl | Q101 |
| 217 | Et | $(CH_2)_3Ph$ | H | H | Cl | Q101 |
| 218 | i-Pr | $(CH_2)_3Ph$ | H | H | Cl | Q101 |
| 219 | H | $(CH_2)_5NHCO_2Me$ | H | H | Br | Q101 |
| 220 | H | $C(Me)H(CH_2)_2$-Q2 | H | H | Br | Q76 |
| 221 | H | $(CH_2)_3$-Q2 | H | H | Br | Q78 |
| 222 | H | $(CH_2)_3$-Q2 | H | H | Br | Q22 |
| 223 | H | $(CH_2)_3$-Q2 | H | H | Br | Q100 |
| 224 | H | $(CH_2)_3$-Q2 | H | H | Br | Q102 |
| 225 | H | $(CH_2)_3$-Q2 | H | H | Br | Ph |
| 226 | Me | $(CH_2)_3$-Q2 | H | H | Br | Q23 |
| 227 | $CH_2CO_2H$ | $(CH_2)_3$-Q2 | H | H | Br | Q23 |
| 228 | H | $(CH_2)_3$—Ph | H | H | Br | Q28 |
| 229 | H | $(CH_2)_3$-Q10 | H | H | Br | Q76 |
| 230 | H | $(CH_2)_3$—Ph | H | H | Br | Q77 |
| 231 | H | $(CH_2)_3$-Q2 | H | H | Br | Q24 |
| 232 | H | $(CH_2)_3$-Q2 | H | H | Br | Q27 |
| 233 | H | $(CH_2)_3$-Q2 | H | H | Br | Q28 |
| 234 | H | $(CH_2)_4Ph$ | H | H | Br | Q23 |
| 235 | H | $(CH_2)_3$-Q11 | H | H | Br | Q76 |
| 236 | H | $(CH_2)_3$-Q2 | H | H | Br | Q103 |
| 237 | H | $(CH_2)_3$-Q2 | H | H | Br | Q79 |
| 238 | $CH_2CO_2Et$ | $(CH_2)_3$-Q2 | H | H | Br | Q23 |
| 239 | H | $(CH_2)_3$-Q2 | H | H | Br | Q23 |
| 240 | H | $(CH_2)_3$-Q2 | H | H | Br | Q46 |
| 241 | H | $(CH_2)_3Ph$ | H | H | CN | Q76 |
| 242 | H | $(CH_2)_3Ph$ | H | H | CN | Q21 |
| 243 | H | $(CH_2)_3Ph$ | H | H | CN | Q23 |
| 244 | H | $(CH_2)_3Ph$ | H | H | CN | Q24 |
| 245 | H | $(CH_2)_3Ph$ | H | H | CN | Q28 |
| 246 | H | $(CH_2)_3Ph$ | H | H | CN | Q30 |
| 247 | H | $(CH_2)_3Ph$ | H | H | CN | Q48 |
| 248 | H | $(CH_2)_3Ph$ | H | H | CN | Q49 |
| 249 | H | $(CH_2)_3Ph$ | H | H | CN | Q68 |
| 250 | H | $(CH_2)_3Ph$ | H | H | CN | Q69 |
| 251 | H | $(CH_2)_3Ph$ | H | H | CN | Q70 |
| 252 | H | $(CH_2)_3Ph$ | H | H | CN | Q71 |
| 253 | H | $(CH_2)_3Ph$ | H | H | CN | Q72 |
| 254 | H | $(CH_2)_3Ph$ | H | H | CN | Q73 |
| 255 | H | $(CH_2)_4Ph$ | H | H | Cl | Q76 |
| 256 | H | $(CH_2)_4Ph$ | H | H | CN | Q76 |
| 257 | H | $(CH_2)_4Ph$ | H | H | Cl | Q21 |
| 258 | H | $(CH_2)_4Ph$ | H | H | Cl | Q23 |
| 259 | H | $(CH_2)_4Ph$ | H | H | Br | Q28 |
| 260 | H | $(CH_2)_4Ph$ | H | H | Br | Q16 |
| 261 | H | $(CH_2)_4Ph$ | H | H | Br | Q17 |
| 262 | H | $(CH_2)_4Ph$ | H | H | Br | Q35 |
| 263 | H | $(CH_2)_4Ph$ | H | H | Br | Q36 |
| 264 | H | $(CH_2)_4Ph$ | H | H | Br | Q71 |
| 265 | H | $(CH_2)_4Ph$ | H | H | Br | Q41 |
| 266 | H | $(CH_2)_4Ph$ | H | H | Br | Q43 |
| 267 | H | $(CH_2)_4Ph$ | H | H | Br | Q44 |
| 268 | H | $(CH_2)_4Ph$ | H | H | Br | Q45 |
| 269 | H | $(CH_2)_4Ph$ | H | H | Cl | Q49 |
| 270 | H | $(CH_2)_4Ph$ | H | H | Cl | Q50 |
| 271 | H | $(CH_2)_4Ph$ | H | H | Cl | Q51 |
| 272 | H | $(CH_2)_4Ph$ | H | H | Cl | Q52 |
| 273 | H | $(CH_2)_4Ph$ | H | H | Cl | Q56 |
| 274 | H | $(CH_2)_4Ph$ | H | H | Cl | Q58 |
| 275 | H | $(CH_2)_4Ph$ | H | H | Cl | Q62 |
| 276 | H | $(CH_2)_4Ph$ | H | H | Cl | Q63 |
| 277 | H | $(CH_2)_3$-Q10 | H | H | Cl | Q76 |
| 278 | H | $(CH_2)_3$-Q10 | H | H | CN | Q76 |
| 279 | Et | $(CH_2)_3$-Q10 | H | H | Br | Q76 |
| 280 | Allyl | $(CH_2)_3$-Q10 | H | H | Br | Q76 |

TABLE I-continued

| No. | R¹ | R² | R³ | R⁴ | X | Ar |
|---|---|---|---|---|---|---|
| 281 | H | (CH₂)₃-Q10 | H | H | Br | Q23 |
| 282 | H | (CH₂)₃-Q10 | H | H | Br | Q29 |
| 283 | H | (CH₂)₃-Q10 | H | H | Br | Q32 |
| 284 | H | (CH₂)₃-Q10 | H | H | Br | Q41 |
| 285 | H | (CH₂)₃-Q10 | H | H | Br | Q45 |
| 286 | H | (CH₂)₃-Q10 | H | H | Br | Q43 |
| 287 | H | (CH₂)₃-Q10 | H | H | Br | Q37 |
| 288 | H | (CH₂)₃-Q10 | H | H | Br | Q38 |
| 289 | H | (CH₂)₃-Q10 | H | H | Br | Q40 |
| 290 | H | (CH₂)₃-Q10 | H | H | Br | Q34 |
| 291 | H | (CH₂)₃-Q10 | H | H | Br | Q33 |
| 292 | H | (CH₂)₃-Q10 | H | H | Br | Q58 |
| 293 | H | (CH₂)₃-Q10 | H | H | Br | Q59 |
| 294 | H | (CH₂)₃-Q10 | H | H | Br | Q55 |
| 295 | H | (CH₂)₃-Q10 | H | H | Br | Q56 |
| 296 | H | (CH₂)₃-Q10 | H | H | Br | Q61 |
| 297 | H | (CH₂)₃-Q10 | H | H | Br | Q60 |
| 298 | H | (CH₂)₃-Q10 | H | H | Br | Q64 |
| 299 | H | (CH₂)₃-Q10 | H | H | Br | Q57 |
| 300 | H | (CH₂)₃-Q10 | H | H | Br | Q63 |
| 301 | H | (CH₂)₃-Q10 | H | H | Br | Q51 |
| 302 | H | (CH₂)₃-Q10 | H | H | Br | Q52 |
| 303 | H | (CH₂)₃-Q10 | H | H | Br | Q53 |
| 304 | H | (CH₂)₃-Q10 | H | H | Br | Q66 |
| 305 | H | (CH₂)₃-Q10 | H | H | Br | Q69 |
| 306 | H | (CH₂)₃-Q10 | H | H | Br | Q74 |
| 307 | H | (CH₂)₃-Q11 | H | H | Cl | Q76 |
| 308 | H | (CH₂)₃-Q11 | H | Me | Cl | Q76 |
| 309 | H | (CH₂)₃-Q11 | Me | H | Br | Q76 |
| 310 | H | (CH₂)₃-Q11 | H | H | CN | Q76 |
| 311 | H | (CH₂)₄-Q11 | H | H | Cl | Q76 |
| 312 | H | (CH₂)₅-Q11 | H | H | Cl | Q76 |
| 313 | H | (CH₂)₈-Q11 | H | H | Cl | Q76 |
| 314 | H | C(Me)H(CH₂)₂-Q11 | H | H | Cl | Q76 |
| 315 | H | (CH₂)₃-Q11 | H | H | Cl | Q23 |
| 316 | H | (CH₂)₃-Q11 | H | H | Cl | Q27 |
| 317 | H | (CH₂)₃-Q11 | H | H | Cl | Q28 |
| 318 | H | (CH₂)₃-Q11 | H | H | Cl | Q31 |
| 319 | H | (CH₂)₅-Q11 | H | H | Cl | Q23 |
| 320 | H | (CH₂)₃-Q11 | H | H | Cl | Q19 |
| 321 | H | (CH₂)₃-Q11 | H | H | Cl | Q45 |
| 322 | H | (CH₂)₃-Q11 | H | H | Cl | Q43 |
| 323 | H | (CH₂)₃-Q11 | H | H | Cl | Q38 |
| 324 | H | (CH₂)₃-Q11 | H | H | Cl | Q39 |
| 325 | H | (CH₂)₃-Q11 | H | H | Cl | Q42 |
| 326 | H | (CH₂)₃-Q11 | H | H | Cl | Q48 |
| 327 | H | (CH₂)₃-Q11 | H | H | Cl | Q62 |
| 328 | H | (CH₂)₃-Q11 | H | H | Cl | Q54 |
| 329 | H | (CH₂)₃-Q11 | H | H | Cl | Q58 |
| 330 | H | (CH₂)₃-Q11 | H | H | Cl | Q59 |
| 331 | H | (CH₂)₃-Q11 | H | H | Cl | Q61 |
| 332 | H | (CH₂)₃-Q11 | H | H | Cl | Q50 |
| 333 | H | (CH₂)₃-Q11 | H | H | Cl | Q51 |
| 334 | H | (CH₂)₃-Q11 | H | H | Cl | Q52 |
| 335 | H | (CH₂)₃-Q11 | H | H | Cl | Q65 |
| 336 | H | (CH₂)₃-Q11 | H | H | Cl | Q67 |
| 337 | H | (CH₂)₃-Q3 | H | H | Cl | Q76 |
| 338 | H | (CH₂)₃-Q2 | H | H | Cl | Q23 |
| 339 | H | (CH₂)₃-Q2 | H | H | Cl | Q28 |
| 340 | H | (CH₂)₃-Q88 | H | H | Cl | Q76 |
| 341 | H | (CH₂)₃-Q88 | H | H | CN | Q76 |
| 342 | H | (CH₂)₃-Q90 | H | H | Cl | Q76 |
| 343 | H | (CH₂)₃-Q90 | H | H | CN | Q76 |
| 344 | H | (CH₂)₃-Q88 | H | H | CN | Q28 |
| 345 | H | (CH₂)₃-Q88 | H | H | Cl | Q17 |
| 346 | H | (CH₂)₃-Q88 | H | H | Cl | Q18 |
| 347 | H | (CH₂)₃-Q90 | H | H | Cl | Q23 |
| 348 | H | (CH₂)₃-Q90 | H | H | Cl | Q16 |
| 349 | H | (CH₂)₃-Q90 | H | H | Cl | Q28 |
| 350 | H | (CH₂)₃-Q91 | H | H | Br | Q76 |
| 351 | H | (CH₂)₃-Q91 | H | H | Br | Q23 |
| 352 | H | (CH₂)₃-Q91 | H | H | Br | Q19 |

TABLE I-continued

| No. | R¹ | R² | R³ | R⁴ | X | Ar |
|---|---|---|---|---|---|---|
| 353 | H | (CH₂)₂N(Me)SO₂Ph | H | H | Cl | Q76 |
| 354 | H | (CH₂)₂N(Me)SO₂-Q2 | H | H | Cl | Q76 |
| 355 | H | (CH₂)₂N(Me)SO₂-Q4 | H | H | Cl | Q76 |
| 356 | H | (CH₂)₂N(Me)SO₂-Q2 | H | H | Br | Q76 |
| 357 | H | (CH₂)₂N(Me)SO₂-Q2 | H | H | CN | Q76 |
| 358 | H | (CH₂)₂N(Me)SO₂Ph | H | H | Cl | Q23 |
| 359 | H | (CH₂)₂N(Me)SO₂-Q2 | H | H | Cl | Q23 |
| 360 | H | (CH₂)₂N(Me)SO₂-Q6 | H | H | Cl | Q23 |
| 361 | H | (CH₂)₂N(Me)SO₂Ph | H | H | Cl | Q24 |
| 362 | H | (CH₂)₂N(Me)SO₂-Q2 | H | H | Cl | Q28 |
| 363 | H | (CH₂)₂N(Me)SO₂Ph | H | H | Cl | Q58 |
| 364 | H | (CH₂)₂N(Me)SO₂Ph | H | H | Cl | Q61 |
| 365 | H | (CH₂)₃N(Me)SO₂Ph | H | H | Br | Q76 |
| 366 | H | (CH₂)₃N(Me)SO₂-Q2 | H | H | Br | Q76 |
| 367 | H | (CH₂)₃N(Me)SO₂-Q5 | H | H | Br | Q76 |
| 368 | H | (CH₂)₂N(Me)SO₂-Q2 | H | H | CN | Q23 |
| 369 | H | (CH₂)₂N(Me)SO₂-Q2 | H | H | CN | Q28 |
| 370 | H | (CH₂)₂N(Me)SO₂-Q3 | H | H | CN | Q23 |
| 371 | H | (CH₂)₃-Q2 | H | H | Br | Q80 |
| 372 | H | (CH₂)₃-Q2 | H | H | Br | Q81 |
| 373 | H | C(Me₂)(CH₂)₂-Q2 | H | H | Br | Q76 |
| 374 | H | CH₂C(Me₂)CH₂-Q2 | H | H | Br | Q76 |
| 375 | H | C(Et₂)(CH₂)₂-Q2 | H | H | Br | Q76 |
| 376 | H | C(n-Pr₂)(CH₂)₂-Q2 | H | H | Br | Q76 |
| 377 | H | C(Me₂)CH₂C(Me₂)-Q2 | H | H | Br | Q76 |
| 378 | H | CH₂C(Et₂)CH₂-Q2 | H | H | Br | Q76 |
| 379 | H | CH₂C(n-Pr₂)CH₂-Q2 | H | H | Br | Q76 |
| 380 | H | (CH₂)₂C(Et₂)-Q2 | H | H | Br | Q76 |
| 381 | H | (CH₂)₂C(n-Pr₂)-Q2 | H | H | Br | Q76 |
| 382 | H | C(Me₂)(CH₂)₃-Q2 | H | H | Br | Q76 |
| 383 | H | CH₂C(Me₂)(CH₂)₂-Q2 | H | H | Br | Q76 |
| 384 | H | (CH₂)₂C(Me₂)CH₂-Q2 | H | H | Br | Q76 |
| 385 | H | (CH₂)₃C(Me₂)-Q2 | H | H | Br | Q76 |
| 386 | H | C(Me₂)(CH₂)₂C(Me₂)-Q2 | H | H | Br | Q76 |
| 387 | H | C(Me₂)CH₂C(Me₂)CH₂-Q2 | H | H | Br | Q76 |
| 388 | H | CH₂C(Me₂)CH₂C(Me₂)-Q2 | H | H | Br | Q76 |
| 389 | H | C(i-Pr₂)(CH₂)₂-Q2 | H | H | Br | Q76 |
| 390 | H | CH₂C(i-Pr₂)CH₂-Q2 | H | H | Br | Q76 |
| 391 | H | (CH₂)₂C(i-Pr₂)-Q2 | H | H | Br | Q76 |
| 392 | H | (CH₂)₃-Q2 | H | H | Br | Q47 |
| 393 | H | CH₂C(Me₂)CH₂Ph | H | H | Br | Q76 |
| 394 | H | CH₂C(Me₂)CH₂CO₂H | H | H | Br | Q76 |
| 395 | H | CH₂C(Me₂)CH₂CO₂Me | H | H | Br | Q76 |
| 396 | H | CH₂C(Me₂)CH₂CN | H | H | Br | Q76 |
| 397 | H | CH₂C(Me₂)CH₂OH | H | H | Br | Q76 |
| 398 | H | CH₂C(Me₂)CH₂OMe | H | H | Br | Q76 |
| 399 | H | CH₂C(Me₂)CH₂-Q98 | H | H | Br | Q76 |
| 400 | H | CH₂C(Me₂)CH₂-Q76 | H | H | Br | Q76 |
| 401 | H | CH₂C(Me₂)CH₂CONEt₂ | H | H | Br | Q76 |
| 402 | H | CH₂C(Me₂)CH₂CO-Q83 | H | H | Br | Q76 |
| 403 | H | CH₂C(Me₂)CH₂CO-Q87 | H | H | Br | Q76 |
| 404 | H | CH₂C(Me₂)CH₂NHSO₂Ph | H | H | Br | Q76 |
| 405 | H | CH₂C(Me₂)CH₂NHSO₂Me | H | H | Br | Q76 |
| 406 | H | CH₂C(Me₂)CH₂N(Me)SO₂Ph | H | H | Br | Q76 |
| 407 | H | CH₂C(Me₂)CH₂N(Me)SO₂Me | H | H | Br | Q76 |
| 408 | H | CH₂C(Me₂)CH₂-Q7 | H | H | Br | Q76 |
| 409 | H | CH₂C(Me₂)CH₂-Q6 | H | H | Br | Q76 |
| 410 | H | CH₂C(Me₂)CH₂-Q10 | H | H | Br | Q76 |
| 411 | H | CH₂C(Me₂)CH₂-Q11 | H | H | Br | Q76 |
| 412 | H | CH₂C(Me₂)CH₂-Q8 | H | H | Br | Q76 |
| 413 | H | CH₂C(Me₂)CH₂-Q9 | H | H | Br | Q76 |
| 414 | H | CH₂C(Me₂)CH₂NHCOPh | H | H | Br | Q76 |
| 415 | H | CH₂C(Me₂)CH₂-Q90 | H | H | Br | Q76 |
| 416 | H | CH₂C(Me₂)CH₂NHCO₂Me | H | H | Br | Q76 |
| 417 | H | CH₂C(Me₂)CH₂N(Me)CO₂Me | H | H | Br | Q76 |
| 418 | H | CH₂C(Me₂)CH₂-Q89 | H | H | Br | Q76 |
| 419 | H | CH₂C(Me₂)CH₂—NEt₂ | H | H | Br | Q76 |
| 420 | H | CH₂C(Me₂)CH₂-Q83 | H | H | Br | Q76 |
| 421 | H | CH₂C(Me₂)CH₂-Q92 | H | H | Br | Q76 |
| 422 | H | CH₂C(Me₂)CH₂-Q94 | H | H | Br | Q76 |

TABLE I-continued

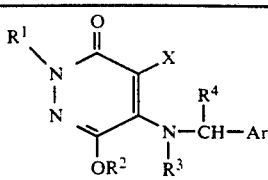

| No. | R¹ | R² | R³ | R⁴ | X | Ar |
|---|---|---|---|---|---|---|
| 423 | H | CH₂C(Me₂)CH₂—OCONHPh | H | H | Br | Q76 |

A method for preparing the compounds of the present invention is explained hereinafter.

The 3(2H)-pyridazinone derivatives of the general formula [I] and pharmaceutically acceptable salts thereof of the present invention can be prepared by the following methods as illustrated by the reaction formulas (1)–(9).

Reaction formula (1)

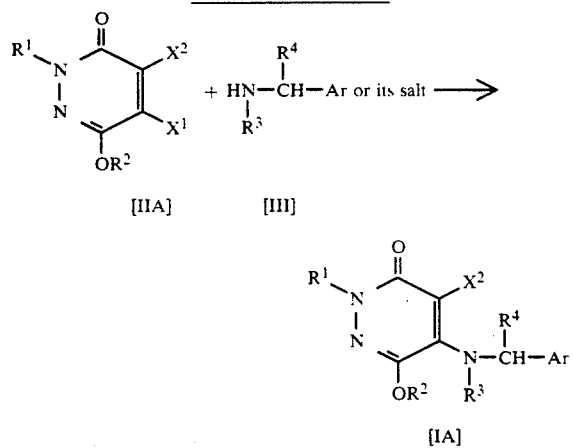

(wherein $X^1$ is a chlorine atom or a bromine atom, $X^2$ is a chlorine atom, a bromine atom or a hydrogen atom, and $R^1$, $R^2$, $R^3$, $R^4$ and Ar are as defined above.)

In the preparation method according to the reaction formula (1), a 4,5-dihalo- or 5-halo-3(2H)-pyridazinone compound of the formula [IIA] is reacted with an arylmethylamine derivative of the formula [III] or its salt optionally in the presence of a dehydrohalogenating agent in an inert solvent to produce a compound of the formula [IA] wherein the 4-position of the compounds of the present invention of the formula [I] is bonded with $X^2$.

In the above reaction formula (1), when $X^2$ in the formula [IIA] is a chlorine atom or a bromine atom, a position isomer of the compound of the formula [IA], i.e. a compound of the formula [VA],

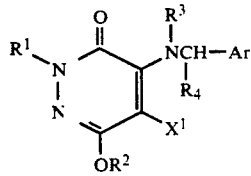

(wherein $R^1$, $R^2$, $R^3$, $R^4$, $X^1$ and Ar are as defined above) having an arylmethylamino group substituted at the 4-position, is formed as a by-product, but the production ratios of the compounds of the formulas [IA] and [VA] depend primarily upon the polarity of the solvent used.

Namely, when a solvent of high polarity is used, the production ratio of the compound [IA] of the present invention tends to be high. Conversely, when a solvent of low polarity (such as benzene, toluene or hexane) is used, the production ratio of the compound [VA] tends to be high.

Therefore, as a solvent suitable for suppressing by-production of the compound of the formula [VA] and for efficient production of the compounds [IA] of the present invention, an ether type solvent (such as tetrahydrofuran or 1,4-dioxane), an amide type solvent (such as formamide, N,N-dimethylformamide, N,N-dimethylacetamide or N-methylpyrrolidone), acetonitrile, dimethylsulfoxide, an alcohol type solvent (such as methanol, ethanol or propanol), an organic amine solvent (such as pyridine, triethylamine, N,N-dimethylaminoethanol or triethanolamine), or water, or a solvent mixture thereof, may be mentioned.

The desired compound of the formula [IA] of the present invention can readily be separated and purified from the mixture of the compounds of the formulas [IA] and [VA] by conventional methods known per se in organic synthesis, such as fractional recrystallization or various silica gel chromatography.

When a compound of the formula [IIA] wherein $X^2$ is a hydrogen atom, i.e. 5-halo-3(2H)-pyridazinone, is used, benzene, toluene, xylene, n-hexane, n-heptane and the like may also be used as a reaction solvent in addition to the above-mentioned solvents.

During the reaction between the compound of the formula [IIA] and the compound of the formula [III], hydrogen chloride or hydrogen bromide is generated. It is usually possible to improve the yield by adding to the reaction system a dehydrohalogenating agent which traps such a hydrogen halide.

Any dehydrohalogenating agent may be used so long as it does not adversely affect the reaction and is capable of trapping a hydrogen halide. As such a dehydrohalogenating agent, an inorganic base such as potassium carbonate, sodium carbonate, potassium hydrogen carbonate, or sodium hydrogen carbonate, or an organic base such as N,N-dimethylaniline, N,N-diethylaniline, trimethylamine, triethylamine, N,N-dimethylaminoethanol or pyridine, may be mentioned.

Otherwise, the starting material arylmethylamine derivative of the formula [III] may be used in an excessive amount as the dehydrohalogenating agent. This gives an improved yield in many cases.

The reaction temperature may be within a range of from 10° C. to the boiling point of the solvent used for the reaction.

The molar ratio of the starting materials may optionally be set. However, the arylmethylamine derivative of the formula [III] or its salt may be used usually in an amount of from 1 to 10 mols, preferably from 1.2 to 5 mols, relative to one mol of the 4,5-dihalo- or 5-halo-3(2H)-pyridazinone derivative of the formula [IIA].

The 4,5-dihalo or 5-halo-3(2H)-pyridazinone derivative of the formula [IIA] can be prepared by a conventional process or by application of a conventional organic reaction as described below.

Namely, the 4,5-dihalo- or 5-halo-3(2H)-pyridazinone derivative of the formula [IIA] can be prepared by the method disclosed in the above-mentioned reference (c).

Among the arylmethylamine derivatives of the formula [III] and their salts in Process (1), those not available as commercial products can be prepared by the method disclosed in Japanese Unexamined Patent Publication No. 267560/1986.

Reaction formula (2)

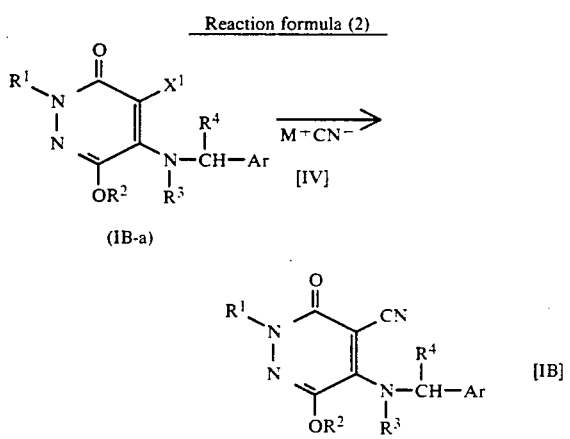

(wherein $R^1$, $R^2$, $R^3$, $R^4$, $X^1$ and Ar are as defined above.)

The above reaction formula (2) illustrates a method for preparing a 4-cyano-5-arylmethylamino derivative of the formula [IB] of the present invention by halogen-substitution reaction between a 4-halo-5-arylmethylamino derivative of the formula [IB-a] and a metal cyanide of the formula [IV].

Examples of metal M include a lithium atom, a sodium atom, a potassium atom, a copper atom and the like.

As a reaction solvent, an amide type solvent such as N,N-dimethylformamide, N,N-dimethylacetamide, N-methylpyrrolidone etc., an alcohol solvent such as methanol, ethanol, n-propanol, n-butanol etc., dimethyl sulfoxide and their water-containing solvents are preferably used.

The reaction temperature varies depending upon the reactants used, but it is usually within a range of from room temperature to the boiling point of the solvent used for the reaction. Generally, the reaction of a bromine atom as a halogen atom at the 4-position proceeds under milder temperature conditions than the reaction of a chlorine atom.

The molar ratio of the starting materials can be optionally determined, and it is sufficient that the metal cyanide of the formula [IV] is used in an amount of from 1.2 to 10 mols relative to one mol of the 4-halo-5-arylmethylamino derivative of the formula [IB-a].

The desired compound can readily be isolated and purified by a method known in organic synthesis such as recrystallization, various silica gel chromatography or distillation.

Reaction formula (3)

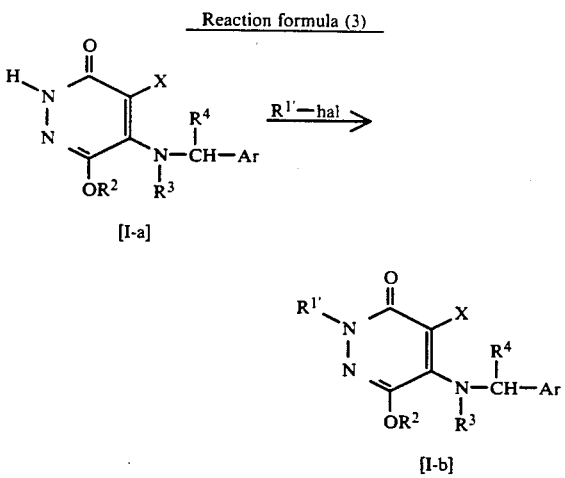

(wherein $R^{1'}$ is a straight chained or branched $C_1$–$C_4$ alkyl group, a $C_3$–$C_4$ alkenyl group or $(CH_2)_nCO_2R^5$, hal is a chlorine atom, a bromine atom, an iodione atom or other eliminatable functional groups, and n, $R^2$, $R^3$, $R^4$, $R^5$, X and Ar are as defined above.)

The above reaction formula (3) illustrates a method for preparing in substitution product at the 2-position of the formula [I-b] of the present invention by reacting a compound of the formula [I-a] wherein the 2-position of the pyridazinone is occupied by a hydrogen atom, among the compounds of the formula [I] of the present invention, with a reactive derivative having an eliminatable group such as a halogeno derivative, an alkyl sulfonate derivative or a phenyl sulfonate derivative as expressed by the formula $R^{1'}$-hal.

The present reaction can be generally conducted in the presence of an inorganic base such as potassium carbonate, sodium carbonate, lithium carbonate, potassium hydrogen carbonate, sodium hydrogen carbonate, lithium hydroxide etc., or an organic base such as triethylamine, tri-n-propylamine etc.

When $R^3$ is an alkyl group in the compound of the formula [I-a], a metal hydride and an organometallic compound such as sodium hydride, n-butyl lithium etc. may be used in addition to the above inorganic bases.

As a reaction solvent, a ketone type solvent (acetone, methyl ethyl ketone, diethyl ketone etc.), an amide type solvent (formamide, N,N-dimethylformamide, N,N-dimethylacetamide etc.), an alcohol type solvent (methanol, ethanol etc.), water and a mixture thereof can be suitably used when an inorganic base or an organic base is used, and an ether type solvent can be suitably used when a metal hydride is used.

In the case of using the inorganic base or the organic base, the reaction temperature is usually within a range of from 0° C. to the boiling point of the solvent, and in the case of using the metal hydride or the organometallic compound, it is usually within a range of from −78° C. to 60° C.

The molar ratio of the starting materials may optionally be determined. However, it is sufficient that the reactive derivative of the formula $R^{1'}$-hal is used in an amount of from 1 to 5 mols relative to one mol of the compound of the formula [I-a].

The desired compound can be isolated and purified in accordance with the method as described with respect to the reaction formula (2).

Reaction formula (4)

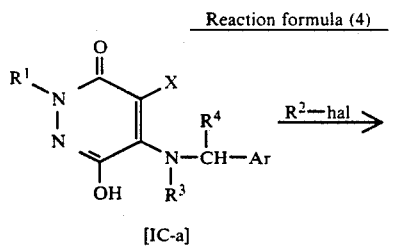

(wherein $R^1$, $R^2$, $R^3$, $R^4$, X, Ar and hal are as defined above.)

The above reaction formula (4) illustrates a method for preparing a compound of the formula [I] of the present invention by reacting a 6-hydroxy-5-arylmethylamino derivative of the formula [IC-a] with a reactive derivative of the formula $R^2$-hal. The 6-hydroxy-5-arylmethyl derivative of the formula [IC-a] used as the starting material in the present reaction can be prepared in accordance with the methods disclosed in the above-mentioned reference (c) and reaction formula (2).

With regard to the reaction conditions, it is possible to employ reaction conditions similar to those in the above reaction formula (3).

Reaction formula (5)

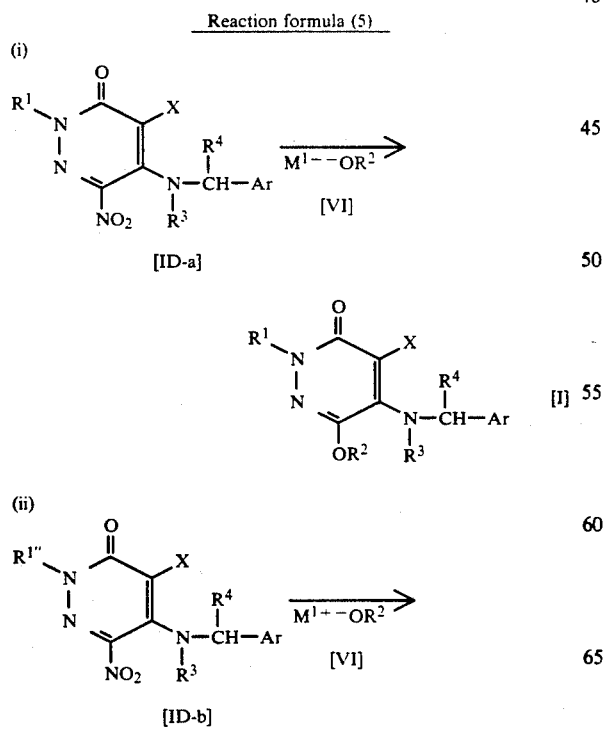

-continued
Reaction formula (5)

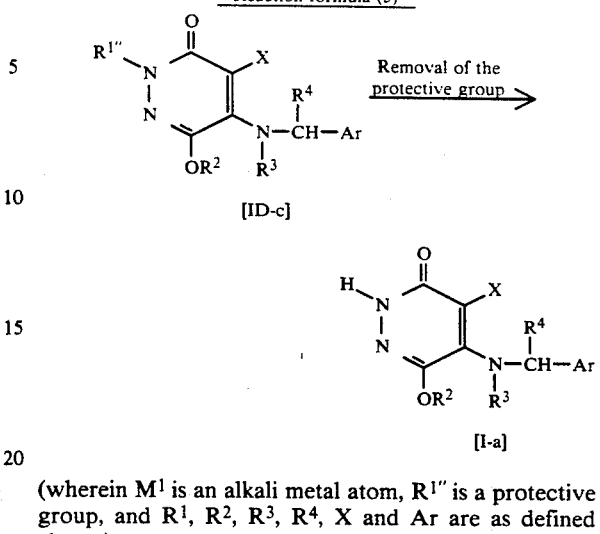

(wherein $M^1$ is an alkali metal atom, $R^{1''}$ is a protective group, and $R^1$, $R^2$, $R^3$, $R^4$, X and Ar are as defined above.)

The above reaction formula (5) illustrates a method for preparing a 6-alkoxy-5-arylmethylamino derivative of the formula [I] or the formula [I-a] of the present invention by substitution reaction of the nitro group of a 6-nitro-5-arylmethylamino derivative of the formula [ID-a] or the formula [ID-b] with an alkali metal alkoxide of the formula [VI]. The 6-nitro derivative of the formula [ID-a] and [ID-b] used as the starting material in the present reaction can be prepared in accordance with the method disclosed in the above-mentioned reference (c).

Among the desired compounds, a compound having hydrogen at 2-position of pyridazinone, can be prepared by the direct route as shown in the reaction formula (5)-(i) wherein $R^1$ of the formula [ID-a] and [I] is hydrogen, or by a route as shown in the reaction formula (5)-(ii) which comprises converting the 6-nitro-5-arylmethylamino derivative of the formula [ID-b] protected at 2-position with $R^{1''}$ to a compound of the formula [ID-c] and then removing the protecting group $R^{1''}$, to obtain the desired compound. The yield is usually better in the latter method in many cases.

As the protective group $R^{1''}$, tetrahydropyranyl, tetrahydrofuranyl, 2-trimethylsilylethoxymethyl ($Me_3$-$SiCH_2CH_2OCH_2$-), pivaloyloxymethyl($Me_3C$-$CO_2CH_2$-), benzyloxymethyl

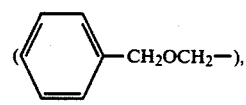

hydroxymethyl, methoxymethyl ($MeOCH_2$-) or $CO_2R$ wherein R is a lower alkyl group, is preferably used.

The removal of the protective group $R^{1''}$ can easily be conducted by a conventional method for the removal of such protective groups.

Here, the alkali metal of the formula $M^1$ includes lithium, sodium and potassium.

Therefore, an alkali metal alkoxide of the formula [VI] used as a nucleophilic agent includes a metal alkoxide as defined by the above $M^1$ and $R^2$.

There is no particular restriction as to the reaction solvent so long as it is inert to the reaction, and there are enumerated an amide type solvent (such as N-methylpyrrolidone, formamide, N,N-dimethylformamide or N,N-dimethylacetamide), an ether type solvent (such as diethyl ether, 1,2-dimethoxyethane, tetrahydrofuran or 1,4-dioxane), a benzene type solvent (such as benzene, toluene or xylene), and a mixture thereof.

The reaction temperature varies depending upon the reactants used. It is usually within a range of from $-15°$ C. to the boiling point of the solvent used for the reaction.

The molar ratio of the starting materials can be optionally determined, and it is sufficient that the alkali meal alkoxide of the formula [VI] is used in an amount of from 1.2 to 10 mols relative to one mol of the 6-nitro-5-arylmethylamino derivative of the formula [ID-a] or the formula [ID-b].

The desired compound can readily be isolated and purified by a method known in organic syntheses such as recrystallization, various silica gel chromatography or distillation.

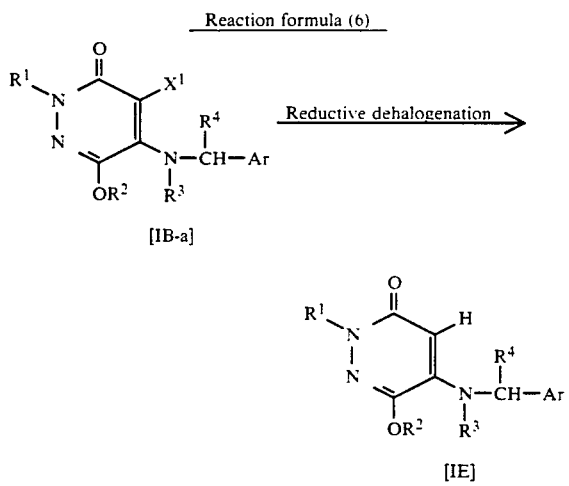

[IB-a]

[IE]

(wherein $R^1$, $R^2$, $R^3$, $R^4$, $X^1$ and Ar are as defined above.)

The above reaction formula (6) illustrates a method for preparing the compound of the formula [IE] of the present invention wherein the 4-position is occupied by hydrogen by reductively removing a halogen atom of the 4-halo derivative of the formula [IB-a].

As the reduction method, catalytic hydrogenation is generally used. As a catalyst, there are enumerated palladium, platinum oxide, Raney nickel and the like, and the reaction proceeds relatively smoothly under a hydrogen pressure of from 1 to 10 atms.

When $R^2$ contains an atom which becomes a catalyst poison, a preferable result is sometimes obtained by using a metal hydride such as tri-n-butyltin hydride or lithium aluminum hydride.

As a reaction solvent, a protonic solvent is used in the case of catalytic hydrogenating reaction, and an ether type solvent is generally used in the case of using a metal hydride.

The reaction temperature may usually be within a range of from $-10°$ C. to 100° C., and the reaction usually proceeds smoothly.

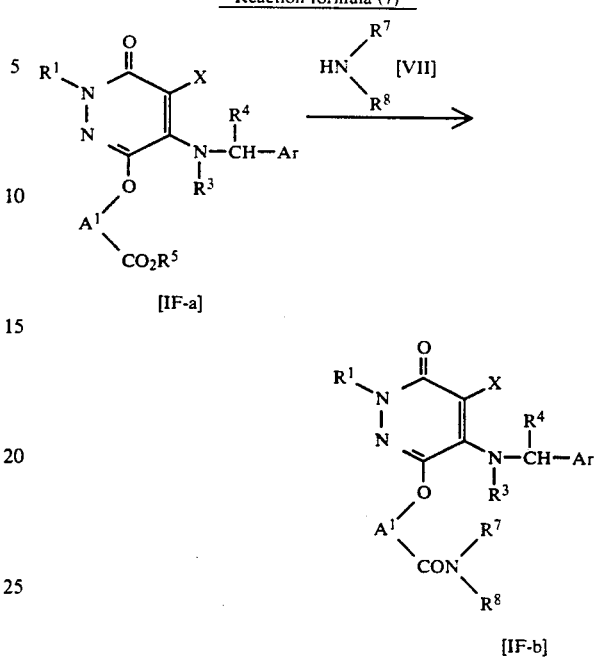

[IF-a]

[IF-b]

(wherein $R^1$, $R^3$, $R^4$, $R^5$, $R^7$, $R^8$, $A^1$, X and Ar are as defined above.)

The above reaction formula (7) illustrates a method for preparing a 6-aminocarbonylalkyleneoxy derivative of the formula [IF-b] by subjecting a 6-ω-carboxyalkyleneoxy derivative or 6-ω-alkoxycarbonylalkyleneoxy derivative of the formula [IF-a] and an amine compound of the formula [VII] to condensation reaction including dehydration or dealcohol.

As a condensation process where $R^5$ is a hydrogen atom, there can be used a condensation method known in peptide synthesis, for example, acid chloride method, mixed acid anhydride method, or a condensation method using a condensation agent such as di-cyclohexylcarbodiimide, carbonyldiimidazole or N-hydroxysuccinic acid imide, and a condensation method is selected depending on the reactivity of amines of the formula [VII]. As a reaction condition, conditions usually used may be employed.

Among amines of the formula [VII], in the reaction with a highly nucleophilic amines, the condensation reaction can proceed even by using esters wherein $R^5$ is an alkyl group. In this case, the solvent is not specially limited and any solvent can be used so long as it does not adversely affect the reaction. In some cases, the reaction can proceed in the absence of a solvent. The reaction temperature is within a range from room temperature to 200° C., more usually from 50° to 150° C.

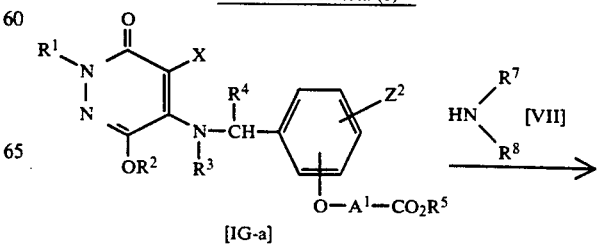

[IG-a]

-continued
Reaction formula (8)

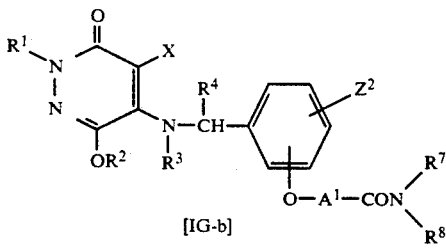

[IG-b]

(wherein $R^1$, $R^2$, $R^3$, $R^4$, $R^5$, $R^7$, $R^8$, X, $Z^2$ and $A^1$ are as defined above.)

The above reaction formula (8) illustrates a method for preparing an amide derivative of the formula [IG-b] by subjecting a 5-(ω-carboxyalkyleneoxy)phenylmethylamino derivative or 5-(ω-alkoxycarbonylalkyleneoxy)phenylmethylamino derivative of the formula [IG-a] and an amine compound of the formula [VII] to condensation reaction.

The present reaction can be carried out in the same manner as in the reaction formula (7).

Reaction formula (9)

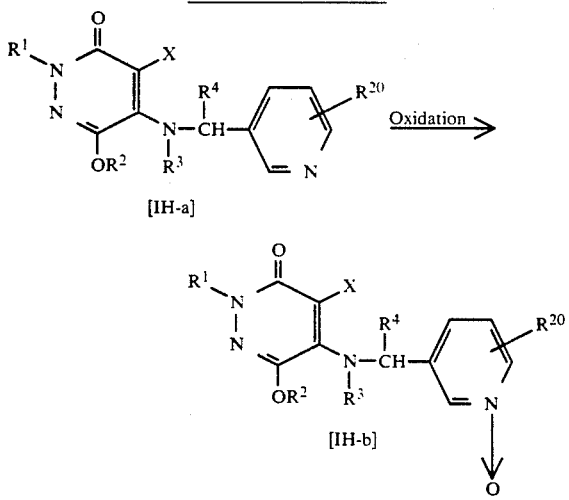

[IH-a]

[IH-b]

(wherein $R^1$, $R^2$, $R^3$, $R^4$, $R^{20}$ and X are as defined above.)

The above reaction formula (9) illustrates a method for preparing an N-oxypyridylmethylamino derivative of the formula [IH-b] by oxidizing a nitrogen atom on the pyridine ring of a 5-pyridylmethylamino derivative of the formula [IH-a]. Examples of an oxidizing agent include performic acid, peracetic acid, perbenzoic acid, metachloroperbenzoic acid, t-butylhydroperoxide, aqueous hydrogen peroxide and the like.

As a reaction solvent, there are enumerated a halogen type solvent (carbon tetrachloride, chloroform, dichloromethane, 1,2-dichloroethane etc.), an ether type solvent (diethyl ether, tetrahydrofuran, 1,4-dioxane etc.), a benzene type solvent (benzene, toluene etc.), an alcohol type solvent (methanol, ethanol, t-butanol etc.), acetic acid, formic acid and the like. In some cases, a transition metal complex may be added as a catalyst.

The reaction temperature may be usually within a range of from −20° C. to the boiling point of the solvent used for the reaction.

The molar ratio of the starting materials may optionally be set, but the oxidizing agent may be used usually in an amount of from 1 to 10 mols, preferably from 1.2 to 5 mols, relative to one mol of the 5-pyridylmethylamino derivative of the formula [IH-a].

The desired compound can readily be isolated and purified by a method known in organic synthesis such as recrystallization, various silica gel chromatography or distillation.

As the manner of administration of the 3(2H)-pyridazinones of the formula [I] or their pharmaceutically acceptable salts of the present invention, there may be mentioned a non-oral administration by injection (subcutaneous, intravenous, intramuscular or intraperitoneal injection), an ointment, a suppository or an aerosol, or an oral administration in the form of tablets, capsules, granules, pills, syrups, liquids, emulsions or suspension.

The above pharmacological composition contains a compound of the present invention in an amount of from about 0.1 to about 99.5% by weight, preferably from about 0.5 to 95% by weight, based on the total weight of the composition.

To the compound of the present invention or to the composition containing the compound of the present invention, other pharmacologically active compounds may be incorporated.

Further, the composition of the present invention may contain a plurality of compounds of the present invention.

The clinical dose of the compound of the present invention varies depending upon the age, the body weight, the sensitivity or the sympton, etc. of the patient. However, the effective daily dose is usually from 0.003 to 1.5 g, preferably from 0.01 to 0.6 g, for an adult.

However, if necessary, an amount outside the above range may be employed.

The compounds of the present invention may be formulated into various suitable formulations depending upon the manner of administration, in accordance with conventional methods commonly employed for the preparation of pharmaceutical formulations.

Namely, tablets, capsules, granules or pills for oral administration, may be prepared by using an excipient such as sugar, lactose, glucose, starch or mannitol; a binder such as syrups, gum arabic, gelatin, sorbitol, tragacanth gum, methyl cellulose or polyvinylpyrrolidone; a disintegrant such as starch, carboxymethyl cellulose or its calcium salts, crystal cellulose powder or polyethylene glycol; a gloss agent such as talc, magnesium or calcium stearate or silica; or a lubricant such as sodium laurate or glycerol.

The injections, solutions, emulsions, suspensions, syrups or aerosols, may be prepared by using a solvent for the active ingredient such as water, ethyl alcohol, isopropyl alcohol, propylene glycol, 1,3-butylene glycol, or polyethylene glycol; a surfactant such as a sorbitan fatty acid ester, a polyoxyethylene sorbitan fatty acid ester, a polyoxyethylene fatty acid ester, a polyoxyethylene ether of hydrogenated castor oil or lecithin, a suspending agent such as a sodium salt of carboxymethyl cellulose, a cellulose derivative such as methyl cellulose, or a natural rubber such as tragacanth gum or gum arabic; or a preservative such as a paraoxy benzoic acid ester, benzalkonium chloride or a salt of sorbic acid.

Likewise, the suppositories may be prepared by using e.g. polyethylene glycol, lanolin or coconut butter.

BEST MODE FOR CARRYING OUT THE INVENTION

Examples (Preparation Examples, Formulation Examples and Test Examples)

Now, the present invention will be described in detail with reference to Examples (including Preparation Examples, Formulation Examples and Test Examples). However, it should be understood that the present invention is by no means restricted by these specific Examples. In Preparation Examples or in Table II, the symbols "NMR", "IR" and "MS" indicate "nuclear magnetic resonance spectrum", "infrared spectrum" and "mass spectrometry", respectively. IR was measured by the potassium bromide disk method, and NMR was measured in heavy hydrogen chloroform, unless otherwise specified.

In the MS data in Table II, only the principal peaks or typical fragment peaks are given.

PREPARATION EXAMPLE 1

4-Chloro-5-(3,4-dimethoxybenzylamino)-6-(5-methoxycarbonylpentyloxy)-3(2H)-pyridazinone (Compound No. 1)

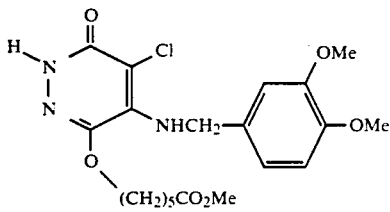

A mixture comprising 4.13 g of 4,5-dichloro-6-(5-methoxycarbonylpentyloxy)-3(2H)-pyridazinone, 6.70 g of 3,4-dimethoxybenzylamine, 130 ml of 1,4-dioxane and 130 ml of water, was refluxed with stirring overnight. The solvent was evaporated under reduced pressure, and water was poured to the residue, whereupon the product was extracted with chloroform. The extract was washed with dilute hydrochloric acid, water and brine in order, and was dried over sodium sulfate. Thereafter, the solvent was distilled off, and the residue was crystallized from chloroform-n-hexane-diethyl ether to obtain 5.28 g of the above identified compound as colorless crystals having a melting point of from 111° C. to 112° C.

NMR δ: 11.71(1H,broad s), 6.71(3H,s), 5.02(1H,collapsed t), 4.76(2H,d), 4.11(2H,t), 3.80(6H,s), 3.57(3H,s), 2.26(2H,t), 2.1–1.2(6H,m).

MS(m/e):439(M+), 404, 151(100%)

PREPARATION EXAMPLE 2

4-Chloro-5-(3,4-dimethoxybenzylamino)-6-(5-carboxypentyloxy)-3(2H)-pyridazinone (Compound No. 2)

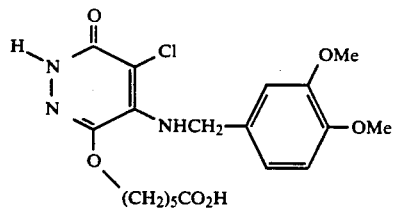

A mixture comprising 240 mg of 4-chloro-5-(3,4-dimethoxybenzylamino)-6-(5-methoxycarbonylpentyloxy)-3(2H)-pyridazinone (Compound No. 1) prepared in Preparation Example 1, 65 mg of sodium hydroxide, 10 ml of methanol and 1 ml of water, was stirred at 60°–70° C. for 1 hour. After the reaction liquor was evaporated under reduced pressure, water was poured to the residue, and the resultant solution was adjusted to pH 1–2 with dilute hydrochloric acid, whereupon the product was extracted with chloroform. The extract was washed with water and brine in order, and was dried over sodium sulfate. Thereafter, the solvent was distilled off, and the residue was crystallized from chloroform-diethyl ether to obtain 192 mg of the above identified compound as colorless crystals having a melting point of from 150.5° C. to 151.5° C.

NMR δ: 6.70(3H,s), 5.14(1H,collapsed t), 4.75(2H,d), 4.10(2H,t), 3.79(6H,s), 2.29(2H,t), 2.0–1.2(6H,m).

IR: ($\nu_{max}^{KBr}$ cm$^{-1}$): 3100, 2910, 1720, 1610.

MS(m/e): 425(M+), 390, 151(100%).

MS(m/e): 425(M+), 390, 151(100%).

PREPARATION EXAMPLE 3

4-Bromo-5-(3-pyridylmethylamino)-6-(3-phenylpropoxy)-3(2H)-pyridazinone hydrochloride (Compound No. 85)

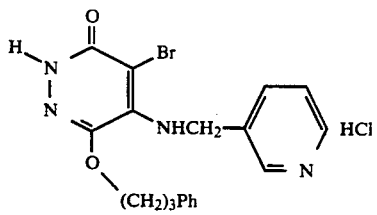

2.50 g of 4-bromo-5-(3-pyridylmethylamino)-6-(3-phenylpropoxy)-3(2H)-pyridazinone (Compound No. 101) was dissolved in 150 ml of a 10% hydrogen chloride methanol solution, and the resultant solution was stirred at room temperature for 1 hour. The solvent was evaporated under reduced pressure, and the residue was crystallized from methanol-diethyl ether to obtain 2.68 g of the above identified compound as colorless crystals having a melting point of from 203° C. to 205° C.

MS(m/e): 414(M+-HCl), 335, 322, 296, 217, 118(100%).

PREPARATION EXAMPLE 4

4-Chloro-5-(3,4-dimethoxybenzylamino)-6-(5-N,N-diethylaminocarbonylpentyloxy)-3(2H)-pyridazinone (Compound No. 12)

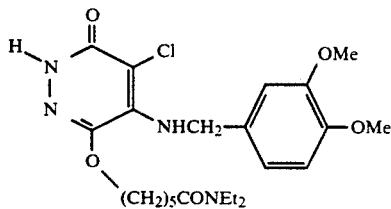

60 mg of ethyl chlorocarbonate was added to a mixture comprising 200 mg of 4-chloro-5-(3,4-dimethoxybenzylamino)-6-(5-carboxypentyloxy)-3(2H)-pyridazinone (Compound No. 2) prepared in Preparation Example 2, 60 mg of triethylamine and 10 ml of tetrahydrofuran under cooling with ice, and the resultant mixture was stirred at the same temperature for 1.5 hours. 100 mg of diethylamine was further added thereto, and the resultant mixture was further stirred for 2.5 hours after removing the ice bath, and the solvent was evaporated under reduced pressure. Water was poured to the residue, and the product was extracted with chloroform. The extract was washed with brine, and was dried over sodium sulfate. Thereafter, the solvent was distilled off, and the residue was crystallized from chloroform-diethyl ether to obtain 209 mg of the above identified compound as colorless crystals having a melting point of from 148° C. to 149.5° C.

NMR δ: 6.75(3H,s), 5.15(1H,collapsed t), 4.79(2H,d), 4.15(2H,t), 3.83(6H,s), 3.81, 3.76(each 2H,q), 2.27(2H,t), 2.1–1.9(6H,m), 1.15, 1.10(each 3H,t).

MS(m/e): 480(M+), 445, 310, 275, 170(100%), 151.

PREPARATION EXAMPLE 5

4-Chloro-5-(3,4-dimethoxybenzylamino)-6-(5-N-methylaminocarbonylpentyloxy)-3(2H)-pyridazinone (Compound No. 8)

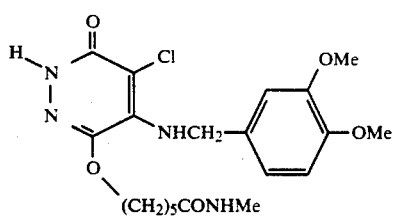

A mixture comprising 200 mg of 4-chloro-5-(3,4-dimethoxybenzylamino)-6-(5-methoxycarbonylpentyloxy)-3(2H)-pyridazinone (Compound No. 1) prepared in Preparation Example 1, 2 ml of 40% methylamine aqueous solution and 6 ml of methanol was refluxed for 8 hours. The reaction mixture was evaporated under reduced pressure, and the product was extracted with chloroform. The extract was washed with water and brine in order, and was dried over sodium sulfate. Thereafter, the solvent was distilled off, and the residue was crystallized from chloroform-diethyl ether to obtain 146 mg of the above identified compound as colorless crystals having a melting point of from 103° C. to 104° C.

NMR δ: 11.65(1H,broad s), 6.73(3H,s), 6.0–5.5(1H,broad m), 5.02(1H,collapsed t), 4.76(2H,d), 4.10(2H,t), 3.81(6H,s), 2.74(3H,d), 2.12(2H, collapsed t), 1.9–1.3(6H,m).

MS(m/e): 438(M+), 403, 310, 274, 151(100%), 128.

PREPARATION EXAMPLE 6

4-Chloro-5-(3-pyridylmethylamino)-6-[5-(1-piperidinocarbonylpentyloxy)]-3(2H)-pyridazinone fumarate (Compound No. 73)

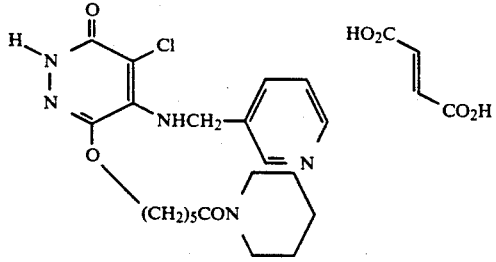

A mixture comprising 1.0 g of 4-chloro-5-(3-pyridylmethylamino)-6-[5-(1-piperidinocarbonylpentyloxy)]-3(2H)-pyridazinone (Compound No. 33), 268 mg of fumaric acid and 20 ml of methanol was stirred at room temperature for 1 hour. The reaction mixture was evaporated under reduced pressure, and the solid residue was crystallized from chloroform-ethylacetate to obtain 1.06 g of the above identified compound as colorless crystals having a melting point of from 156° C. to 158° C.

MS(m/e): 433[M+-(CH-CO₂H)₂], 398, 287, 251, 216, 182(100%).

PREPARATION EXAMPLE 7

4-Cyano-5-(3-pyridylmethylamino)-6-[3-(4-chlorophenylpropoxy)]-3(2H)-pyridazinone (Compound No. 107)

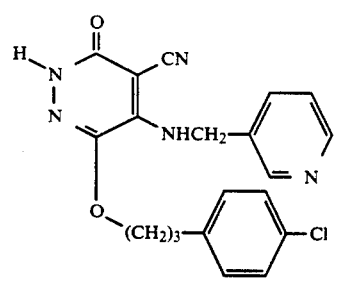

A mixture comprising 1.0 g of 4-bromo 5-(3-pyridylmethylamino)-6-[3-(4-chlorophenylpropoxy)]-3-(2H)-pyridazinone (Compound No. 106), 587 mg of copper cyanide and 20 ml of N-methylpyrrolidone was stirred at 120°–130° C. for 6 hours. After cooling the resultant mixture to room temperature, a saturated ammonium chloride aqueous solution was added thereto, whereupon the product was extracted with chloroform. The extract was washed with brine, and was dried over sodium sulfate. Thereafter, the solvent was distilled off, and the residue was crystallized from acetonitrile to obtain 313 mg of the above identified compound as slightly yellow crystals having a melting point of from 188° C. to 190° C.

MS(m/e): 395(M+), 350, 243, 152(100%), 124.

IR: ($v_{max}^{KBr}$ cm$^{-1}$): 3100, 2850, 2200, 1620.

PREPARATION EXAMPLE 8

2-Ethoxycarbonylmethyl-4-bromo-5-(3,4-dimethoxybenzylamino)-6-[3-(4-chlorophenylpropoxy)]-3(2H)-pyridazinone (Compound No. 238)

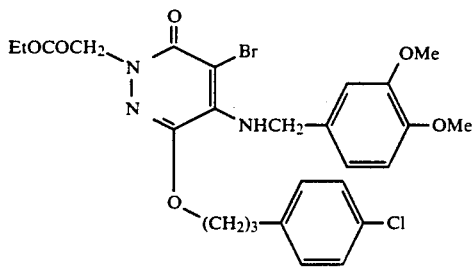

A mixture comprising 100 mg of 4-bromo-5-(3,4-dimethoxybenzylamino)-6-[3-(4-chlorophenylpropoxy)]-3(2H)-pyridazinone (Compound No. 239), 33 mg of potassium carbonate, 49 mg of ethyl bromoacetate, 316 mg of sodium iodine and 5 ml of methyl ethyl ketone, was stirred under reflux for 5 hours. After removing the undissolved material by filtration, the solvent was evaporated under reduced pressure, and water was poured to the residue, whereupon the product was extracted with chloroform. The extract was washed with brine, and was dried over sodium sulfate. Thereafter, the solvent was distilled off, and the residue was purified by silica gel column chromatography (elute n-hexane/ethyl acetate=1/1) to obtain 82 mg of the above identified compound as colorless oil.

MS(m/e): 593(M+), 514, 288, 259, 151(100%).

PREPARATION EXAMPLE 9

2-(Carboxymethyl)-4-bromo-5-(3,4-dimethoxybenzylamino)-6-[3-(4-chlorophenylpropoxy)]-3(2H)-pyridazinone (Compound No. 227)

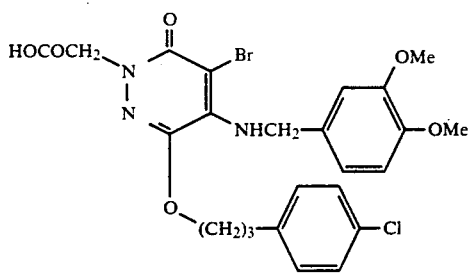

A mixture comprising 80 mg of 2-ethoxycarbonylmethyl-4-bromo-5-(3,4-dimethoxybenzylamino)-6-[3-(4-chlorophenylpropoxy)]-3(2H)-pyridazinone (Compound No. 238) prepared in Preparation Example 8, 16 mg of sodium hydroxide, 2 ml of methanol and 0.2 ml of water, was stirred at room temperature for 2 hours. After the reaction liquor was evaporated under reduced pressure, water was poured to the residue, and the resultant solution was adjusted to pH 1-2 with dilute hydrochloric acid, whereupon the product was extracted with chloroform. The extract was washed with brine, and was dried over sodium sulfate. Thereafter, the solvent was distilled off, and the residue was crystallized from chloroform-diethyl ether to obtain 49 mg of the above identified compound as colorless crystals having a melting point of from 140° C. to 141° C.

MS(m/e): 486(M+-Br), 427, 371, 151(100%).

PREPARATION EXAMPLE 10

4-Bromo-5-[3-(N-oxypyridylmethylamino)]-6-(3-phenylpropoxy)-3(2H)-pyridazinone (Compound No. 230)

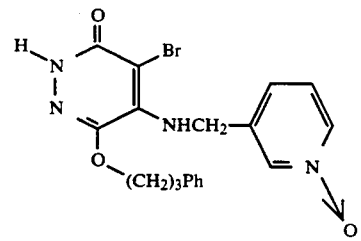

A mixture comprising 250 mg of 4-bromo-5-(3-pyridylmethylamino)-6-(3-phenylpropoxy)-3(2H)-pyridazinone, 167 mg of meta-chloroperbenzoic acid, and 10 ml of dichloromethane, was stirred at room temperature for 6 hours. To the resultant mixture, were added a saturated sodium hydrogencarbonate aqueous solution and chloroform, and the organic layer was separated. The remaining aqueous layer was reextracted with chloroform, and this extract was combined with the former organic layer. The combined extract was washed with water and brine in order, and was dried over sodium sulfate. Thereafter, the solvent was distilled off, and the resulting solid residue was crystallized from chloroform-diethyl ether to obtain the above identified compound as colorless crystals having a melting point of from 191° C. to 192° C.

MS(m/e): 414(M+-0), 335, 323, 295, 217, 91(100%).

Compounds described in the following Table II were prepared in accordance with the above Preparation Examples. The structures of the compounds should be referred to Compound Numbers as shown in Table I. The most right column of Table II indicates Preparation Example Numbers applied.

TABLE II

| Compound No. | Melting point (°C.) | MS (m/e) | Example No. |
|---|---|---|---|
| 1 | 111~112 | see Example 1 | 1 |
| 2 | 150.5~151.5 | see Example 2 | 1 |
| 3 | 111.5~112.5 | 380(M+), 345(100%) | 1 |
| 4 | 195~195.5 | 366(M+), 92(100%) | 2 |
| 5 | 171~172 | 338(M+), 92(100%) | 1 |
| 6 | 240~240.5 | 292(M+-H₂O), 92(100%) | 2 |
| 7 | 194~198 | 324(M+-HCl), 92(100%) | 3 |
| 8 | 103~104 | see Example 5 | 5 |
| 9 | 179~180 | 452(M+), 151(100%) | 4 |
| 10 | 167~167.5 | 424(M+), 151(100%) | 4 |
| 11 | 164~165 | 494(M+), 184(100%) | 4 |
| 12 | 148~149.5 | see Example 4 | 4 |
| 13 | 155~156 | 520(M+), 210(100%) | 4 |
| 14 | 135.5~136.5 | 425(M+), 151(100%) | 1 |
| 15 | 167~168.5 | 397(M+), 151(100%) | 2 |
| 16 | 163~164 | 424(M+), 151(100%) | 4 |
| 17 | 136~138 | 452(M+), 151(100%) | 4 |
| 18 | 181~181.5 | 466(M+), 155(100%) | 4 |
| 19 | 167~168 | 397(M+), 151(100%) | 1 |

TABLE II-continued

| Compound No. | Melting point (°C.) | MS (m/e) | Example No. |
|---|---|---|---|
| 20 | 192~194 | 369(M+), 151(100%) | 2 |
| 21 | 182~185 | 542(M+), 151(100%) | 1 |
| 22 | 163~165 | 483(M+), 92(100%) | 1 |
| 23 | 200~201 | 494(M+), 151(100%) | 1 |
| 24 | Solid | 435(M+), 217(100%) | 1 |
| 25 | 108~108.5 | 508(M+), 198(100%) | 4 |
| 26 | 189~190 | 492(M+), 182(100%) | 4 |
| 27 | 201~201.5 | 478(M+), 168(100%) | 4 |
| 28 | 163~164 | 421(M+), 170(100%) | 4 |
| 29 | 173~175 | 393(M+), 142(100%) | 4 |
| 30 | 108.5~109 | 467(M+), 151(100%) | 1 |
| 31 | 132.5~133 | 418(M+-Cl), 151(100%) | 1 |
| 32 | 165~166 | 419(M+), 168(100%) | 4 |
| 33 | 173.5~176 | 433(M+), 182(100%) | 4 |
| 34 | 169.5~170 | 480(M+), 170(100%) | 4 |
| 35 | 145~146.5 | 508(M+), 198(100%) | 4 |
| 36 | 127~128 | 536(M+), 226(100%) | 4 |
| 37 | 162~163 | 506(M+), 151(100%) | 4 |
| 38 | 163.5~164 | 520(M+), 151(100%) | 4 |
| 39 | 157.5~158 | 522(M+), 151(100%) | 4 |
| 40 | 145~145.5 | 423(M+), 135(100%) | 1 |
| 41 | 125~126 | 483(M+), 151(100%) | 1 |
| 42 | 166~167 | 469(M+), 151(100%) | 2 |
| 43 | 144~144.5 | 496(M−), 151(100%) | 4 |
| 44 | 180~180.5 | 522(M+), 151(100%) | 4 |
| 45 | 161~161.5 | 536(M+), 151(100%) | 4 |
| 46 | 114~116 | 524(M+), 170(100%) | 4 |
| 47 | 136~137 | 552(M+), 198(100%) | 4 |
| 48 | 135~136 | 538(M+), 151(100%) | 4 |
| 49 | 157~158 | 409(M+), 135(100%) | 2 |
| 50 | 153~155 | 464(M+), 151(100%) | 4 |
| 51 | 114~116 | 461(M−), 217(100%) | 4 |
| 52 | Hygroscopic solid | 461(M+-HCl), 217(100%) | 3 |
| 53 | 103~104 | 436(M+), 135(100%) | 4 |
| 54 | 123~124 | 464(M−), 170(100%) | 4 |
| 55 | 124~125 | 492(M+), 198(100%) | 4 |
| 56 | 148~149 | 462(M−), 168(100%) | 4 |
| 57 | 144~145 | 476(M+), 182(100%) | 4 |
| 58 | 121~122 | 478(M−), 135(100%) | 4 |
| 59 | 121~122 | 432(M+-Br), 151(100%) | 1 |
| 60 | 118~119 | 478(M+), 151(100%) | 4 |
| 61 | 187~187.5 | 506(M+), 196(100%) | 4 |
| 62 | 165.5~166 | 534(M−), 98(100%) | 4 |
| 63 | 156.5~157 | 524(M+), 170(100%) | 4 |
| 64 | 133~133.5 | 552(M+), 198(100%) | 4 |
| 65 | 116~116.5 | 580(M+), 226(100%) | 4 |
| 66 | 148.5~150 | 550(M+), 196(100%) | 4 |
| 67 | 150~151 | 564(M+), 210(100%) | 4 |
| 68 | 141~142 | 566(M+), 487(100%) | 4 |
| 69 | 87~89 | 419(M+), 84(100%) | 4 |
| 70 | Solid | 463(M+), 84(100%) | 4 |
| 71 | 112~114 | 478(M+), 168(100%) | 4 |
| 72 | 170~173 | 433(M+-HCl), 182(100%) | 3 |
| 73 | 156~158 | see Example 6 | 6 |
| 74 | 160~162 | 461(M+), 210(100%) | 4 |
| 75 | Hygroscopic solid | 461(M+-HCl), 210(100%) | 3 |
| 76 | 135~137 | 461[M+-(CH—CO₂H)₂], 210(100%) | 6 |
| 77 | 142~144 | 433(M+), 182(100%) | 4 |
| 78 | Hygroscopic solid | 405(M+-HCl), 153(100%) | 3 |
| 79 | Hygroscopic solid | 433(M+-HCl), 182(100%) | 3 |
| 80 | 178~181 | 400(M+-HCl), 105(100%) | 3 |
| 81 | Hygroscopic solid | 419(M+-HCl), 168(100%) | 3 |
| 82 | Hygroscopic solid | 463(M+-HCl), 168(100%) | 3 |
| 83 | 121~123 | 459(M+), 380(100%) | 1 |
| 84 | 154~156 | 473(M+), 394(100%) | 1 |
| 85 | 203~205 | see Example 3 | 3 |
| 86 | 133~134 | 588(M+), 278(100%) | 4 |
| 87 | 95~96 | 616(M+), 180(100%) | 4 |
| 88 | 106~107 | 528(M+ -Q83), 154(100%) | 1 |
| 89 | 211~212 | 410(M+), 92(100%) | 2 |
| 90 | 152~154 | 429(M+), 151(100%) | 1 |
| 91 | 134~135 | 370(M+), 91(100%) | 1 |
| 92 | 190~202 | 370(M+-HCl), 91(100%) | 3 |
| 93 | 166~172 | 370[M+-(CH—CO₂H)₂], 91(100%) | 6 |
| 94 | 105~106 | 380, 182(100%) | 1 |
| 95 | 145.5~146 | 211(100%), 141 | 1 |
| 96 | 155~156 | 276, 211(100%) | 1 |
| 97 | 169~170 | 296, 211(100%) | 1 |
| 98 | 132~132.5 | 515(M+-Br), 170(100%) | 1 |
| 99 | 149~150 | 535(M+), 170(100%) | 1 |
| 100 | 142~143 | 211(100%), 141 | 1 |
| 101 | 130~133 | 414(M+), 91(100%) | 1 |
| 102 | 118~119 | 428(M+), 91(100%) | 1 |
| 103 | 146~147 | 408(M+-Br), 151(100%) | 1 |
| 104 | 203~205 | 471(M+), 106(100%) | 1 |
| 105 | 153.5~154 | 404(M+), 125(100%) | 1 |
| 106 | 148~150 | 448(M+), 151(100%) | 1 |
| 107 | 188~190 | see Example 7 | 7 |
| 108 | 156.5~157 | 480(M+), 126(100%) | 1 |
| 109 | 142~143 | 522(M+), 126(100%) | 1 |
| 110 | 139.5~140 | 421(M+), 126(100%) | 1 |
| 111 | 173~174 | 435(M+), 140(100%) | 1 |
| 112 | 142.5~144 | 494(M+), 140(100%) | 1 |
| 113 | 209~214 | 485(M+-HCl), 190(100%) | 3 |
| 114 | 173~175 | 296[M+-(CH₂)₃CONHPh], 161(100%) | 4 |
| 115 | 218.5~219 | 205[M+-((CH₂)₃CON-Q96, CH₂-Q23)], 151(100%) | 4 |
| 116 | 233~234 | 205[M+-(CH₂)₃CONH-Q97], 151(100%) | 4 |
| 117 | 216~216.5 | 551(M+), 151(100%) | 4 |
| 118 | 132~134 | 437(M+), 142(100%) | 4 |
| 119 | 131~132 | 505(M+), 210(100%) | 4 |
| 120 | 129~130 | 354[M+-(CH₂)₃CONMe-Q2], 151(100%) | 4 |
| 121 | 97~104 | 499(M+-HCl), 204(100%) | 3 |
| 122 | 141~144 | 392(M+-Br), 76(100%) | 4 |
| 123 | 105~110 | 513(M+-HCl), 218(100%) | 3 |
| 124 | 153~155 | 485(M+), 190(100%) | 4 |
| 125 | 110~111 | 572(M+), 218(100%) | 4 |
| 126 | 186~193 | 479(M+-HCl), 184(100%) | 3 |
| 127 | 199~201 | 451(M+), 156(100%) | 4 |
| 128 | 176~176.5 | 568(M+), 258(100%) | 4 |
| 129 | 145~147 | 471(M+), 105(100%) | 1 |
| 130 | 164~165 | 530(M+), 151(100%) | 4 |
| 131 | 101~103 | 463(M+), 98(100%) | 1 |
| 132 | 137~140 | 449(M+), 98(100%) | 1 |
| 133 | 152~152.5 | 522(M+), 151(100%) | 1 |
| 134 | 123~123.5 | 477(M+), 398(100%) | 1 |
| 135 | Amorphous | 463(M+-HCl), 168(100%) | 3 |
| 136 | 142~143 | 459(M+), 45(100%) | 1 |
| 137 | 129.5~131 | 522(M+), 168(100%) | 1 |
| 138 | 192~193.5 | 431(M+), 136(100%) | 1 |
| 139 | 119~119.5 | 439(M+-Br), 151(100%) | 1 |
| 140 | 168~170 | 490(M+), 151(100%) | 1 |
| 141 | 192.5~194 | 493(M+), 198(100%) | 1 |
| 142 | 103~109 | 521(M+), 184(100%) | 1 |
| 143 | 164~165 | 473(M+-Br), 151(100%) | 1 |
| 144 | 142~143 | 501(M+-Br), 151(100%) | 1 |
| 145 | 168~169 | 445(M+), 122(100%) | 1 |
| 146 | 107~108 | 473(M+), 98(100%) | 1 |
| 147 | 179~180 | 504(M+), 151(100%) | 1 |
| 148 | 138.5~139 | 453(M+-Br), 151(100%) | 1 |
| 149 | 139~139.5 | 393(M+-OMe), 98(100%) | 1 |
| 150 | 134~136 | 439(M+), 92(100%) | 1 |
| 151 | 190~191 | 411(M+), 116(100%) | 1 |
| 152 | 153~154 | 484(M+), 151(100%) | 1 |
| 153 | 97~99 | 498(M+), 151(100%) | 1 |
| 154 | 107~108 | 439(M+), 144(100%) | 1 |
| 155 | 102.5~104 | 453(M+), 102(100%) | 1 |
| 156 | 122~123 | 425(M+), 130(100%) | 1 |
| 157 | 106.5~107 | 498(M+), 151(100%) | 1 |
| 158 | 134.5~136 | 512(M+), 151(100%) | 1 |
| 159 | 123~124.5 | 451(M+), 100(100%) | 1 |
| 160 | 129~130 | 465(M+), 386(100%) | 1 |
| 161 | Oily substance | 437(M+), 142(100%) | 1 |
| 162 | 139~140 | 524(M+), 151(100%) | 1 |
| 163 | 133~134.5 | 496(M+), 151(100%) | 1 |
| 164 | 135~142 | 395[M+-(NHPh, HCl)], | 3 |

TABLE II-continued

| Compound No. | Melting point (°C.) | MS (m/e) | Example No. |
|---|---|---|---|
| 165 | 170~177 | 398[M$^+$-(CONHPh, HCl)], 119(100%) | 3 |
| 166 | 188~205 | 448(M$^+$-HCl), 151(100%) | 3 |
| 167 | 184~190 | 404(M$^+$-HCl), 125(100%) | 3 |
| 168 | 153~156 | 418(M$^+$), 125(100%) | 1 |
| 169 | 160~161 | 448[M$^+$-(CH—CO$_2$H)$_2$], 151(100%) | 6 |
| 170 | 155~156 | 448[M$^+$-½(HC(OH)CO$_2$H)$_2$], 151(100%) | 6 |
| 171 | 163~165 | 448[M$^+$-½(CH—CO$_2$H)$_2$], 151(100%) | 6 |
| 172 | 178.5~179.5 | 448[M$^+$-½(CO$_2$H)$_2$], 151(100%) | 6 |
| 173 | 112~114 | 444(M$^+$), 148(100%) | 1 |
| 174 | 130~131 | 458(M$^+$), 121(100%) | 1 |
| 175 | 103~105 | 472(M$^+$), 121(100%) | 1 |
| 176 | 124~126 | 428(M$^+$), 121(100%) | 1 |
| 177 | 150~152 | 424(M$^+$-Br), 151(100%) | 1 |
| 178 | 152~154 | 487(M$^+$-Br), 184(100%) | 1 |
| 179 | 103~105 | 539(M$^+$), 132(100%) | 1 |
| 180 | 147~151 | 460(M$^+$), 164(100%) | 1 |
| 181 | 205~215 | 476(M$^-$-HCl), 217(100%) | 1 |
| 182 | 129~131 | 474(M$^+$), 178(100%) | 1 |
| 183 | 169~170 | 533(M$^+$), 151(100%) | 1 |
| 184 | 126~127 | 502(M$^+$), 164(100%) | 1 |
| 185 | 109~111 | 561(M$^+$), 151(100%) | 1 |
| 186 | 131~132 | 502(M$^-$), 164(100%) | 1 |
| 187 | 103~105 | 561(M$^-$), 151(100%) | 1 |
| 188 | 188~190 | 460(M$^+$), 164(100%) | 1 |
| 189 | 163.5~164 | 519(M$^-$), 151(100%) | 1 |
| 190 | 85.5~86 | 444(M$^-$), 148(100%) | 1 |
| 191 | 187~188 | 472(M$^+$), 147(100%) | 1 |
| 192 | 149~150.5 | 561(M$^-$), 151(100%) | 1 |
| 193 | 206~210 | 420(M$^-$-HCl), 97(100%) | 3 |
| 194 | 209~210 | 420(M$^-$), 97(100%) | 1 |
| 195 | 138~142 | 479(M$^-$), 151(100%) | 1 |
| 196 | 143~145 | 415(M$^-$), 336(100%) | 1 |
| 197 | 152.5~153 | 474(M$^-$), 151(100%) | 1 |
| 198 | 91~96 | 416(M$^-$), 337(100%) | 1 |
| 199 | 168~168.5 | 475(M$^-$), 151(100%) | 1 |
| 200 | 134~134.5 | 405(M$^-$), 92(100%) | 1 |
| 201 | 130.5~131 | 464(M$^-$), 151(100%) | 1 |
| 202 | 116~126 | 452(M$^-$), 151(100%) | 3 |
| 203 | 110~120 | 442(M$^+$), 58(100%) | 3 |
| 204 | 179~184 | 454(M$^-$-HCl), 86(100%) | 3 |
| 205 | 115~120 | 571(M$^-$), 151(100%) | 3 |
| 206 | 127~132 | 605(M$^-$), 151(100%) | 3 |
| 207 | 160~168 | 567(M$^-$-Br), 151(100%) | 3 |
| 208 | 150~151 | 413(M$^-$), 135(100%) | 1 |
| 209 | 144~146 | 464(M$^-$), 135(100%) | 1 |
| 210 | 162~163 | 428(M$^+$), 91(100%) | 1 |
| 211 | 181~182 | 427(M$^-$), 135(100%) | 1 |
| 212 | 145~146 | 519(M$^+$), 135(100%) | 1 |
| 213 | 156~165 | 589(M$^+$), 135(100%) | 3 |
| 214 | 176~179 | 252[M$^+$-CH$_2$C(Me$_2$)CH$_2$-Q$_2$], 125(100%) | 3 |
| 215 | 167~168 | 392(M$^+$-Br), 135(100%) | 1 |
| 216 | 190~192 | 447(M$^+$), 135(100%) | 1 |
| 217 | Oily substance | 441(M$^+$), 135(100%) | 8 |
| 218 | 97~98 | 455(M$^+$), 135(100%) | 8 |
| 219 | 147~148 | 481(M$^+$), 135(100%) | 1 |
| 220 | 174~177 | 462(M$^+$), 125(100%) | 1 |
| 221 | 131~132 | 482(M$^+$), 125(100%) | 1 |
| 222 | 151~153 | 432(M$^+$), 155(100%) | 1 |
| 223 | 141~144 | 438(M$^+$), 81(100%) | 1 |
| 224 | 168~169 | 418(M$^+$-Br)(100%) | 1 |
| 225 | 149~152 | 461(M$^+$), 382(100%) | 1 |
| 226 | Oily substance | 521(M$^+$), 151(100%) | 8 |
| 227 | 140~141 | see Example 9 | 9 |
| 228 | 108~108.5 | 515(M$^+$), 193(100%) | 1 |
| 229 | 203~205 | 471(M$^+$), 106(100%) | 1 |
| 230 | 191~192 | see Example 10 | 10 |
| 231 | 123~125 | 521(M$^+$), 105(100%) | 1 |
| 232 | 112~113 | 549(M$^+$), 471(100%) | 1 |
| 233 | 113~115 | 549(M$^+$), 471(100%) | 1 |
| 234 | 146~147 | 408(M$^+$), 151(100%) | 1 |
| 235 | 178~181 | 492(M$^+$), 121(100%) | 1 |
| 236 | 178~181 | 527(M$^+$), 171(100%) | 1 |
| 237 | 185~189 | 399(M$^+$-Br), 122(100%) | 1 |
| 238 | Oily substance | see Example 8 | 8 |
| 239 | 153~154 | 428(M$^+$-Br), 151(100%) | 1 |
| 240 | Oily substance | 518(M$^+$-Br), 105(100%) | 1 |

FORMULATION EXAMPLE 1 (Tablets)

| | |
|---|---|
| Compound No. 85 | 10 g |
| Lactose | 20 g |
| Starch | 4 g |
| Starch for paste | 1 g |
| Magnesium stearate | 0.1 g |
| Carboxymethyl cellulose calcium | 7 g |
| Total | 42.1 g |

The above components were mixed in a usual manner, and formulated into sugar-coated tablets each containing 50 mg of an active ingredient.

FORMULATION EXAMPLE 2 (Capsules)

| | |
|---|---|
| Compound No. 88 | 10 g |
| Lactose | 20 g |
| Microcrystal cellulose | 10 g |
| Magnesium stearate | 1 g |
| Total | 41 g |

The above components were mixed in a usual manner, and filled into gelatin capsules to obtain capsules each containing 50 mg of an active ingredient.

FORMULATION EXAMPLE 3 (Soft capsules)

| | |
|---|---|
| Compound No. 94 | 10 g |
| Corn oil | 35 g |
| Total | 45 g |

The above components were mixed and formulated in a usual manner to obtain soft capsules.

FORMULATION EXAMPLE 4 (Ointment)

| | |
|---|---|
| Compound No. 55 | 1.0 g |
| Olive oil | 20 g |
| White vaseline | 79 g |
| Total | 100 g |

The above components were mixed in a usual manner to obtain 1% ointment.

FORMULATION EXAMPLE 5 (Aerosol suspension)

| | |
|---|---|
| (A) Compound No. 11 | 0.25% |
| Isopropyl myristate | 0.10% |
| Ethanol | 26.40% |
| (B) A 60-40% mixture of 1,2-dichlorotetrafluoroethane and | 73.25% |

-continued

| |
|---|
| 1-chloropentafluoroethane |

The above composition (A) was mixed. The solution mixture thereby obtained was charged in a container equipped with a valve, and the propellant (B) was injected from the valve nozzle to a gauge pressure of from about 2.46 to 2.81 mg/$cm^2$ to obtain an aerosol suspension.

Test Method

I. Anti-platelet aggregation effect

1. In vitro test (A) Anti-platelet aggregation effect in rabbits

Blood was collected from the central artery of Japanese white male rabbits (weight: 1.8 to 2.5 kg) into a syringe containing 1/10 volume 3.8% sodium citrate. The blood thus obtained was subjected to a centrifuge at 200×g for 7 minutes at room temperature to obtain platelet rich plasma (PRP). Furthermore, the residue was subjected to a centrifuge at 2000×g for 10 minutes to obtain platelet poor plasma (PPP). The measurement was effected by diluting PRP and PPP to 300,000/$mm^3$. PRP and PPP were placed in a cuvette, and the measurement range of transmittance was adjusted to 0% in the case of PRP and to 100% in the case of PPP. Thereafter, a test sample drug dissolved in 100% dimethylsulfoxide (DMSO) was added to PRP (the final concentration of DMSO: 0.25%). After incubation was effected at 37° C., 900 rpm for 2 minutes, an aggregating agent was added to measure an aggregation curve. The anti-platelet aggregation effect of the test sample drug was expressed by a concentration ($IC_{50}$: μM) at which the aggregation of control sample was 50% inhibited. The aggregating agents ADP and arachidonic acid (A.A) were used at minimum concentrations (ADP: 5 to 10 μM: A.A.: 0.2 to 0.3 mM) which caused maximum aggregation. The measurement of platelet aggregation was carried out by using NBS HEMA TRACER 601.

(B) Anti-platelet aggregation effect in guinea-pigs

Blood was collected from the central artery of a Hartley type male guinea-pig (weight: about 300 g) in the same manner as above, and was subjected to a centrifuge at 160×g for 10 minutes at room temperature to obtain PRP. Furthermore, the residue was subjected to a centrifuge at 3000×g for 15 minutes. PRP for measurement was prepared in the same manner as in the above rabbit test example, and a test sample drug dissolved in 100% DMSO was added (DMSO final concentration: 0.5%) to calculate 50% aggregation-inhibiting concentration $IC_{50}$ value to a control sample. As the aggregating agent, A.A having the final concentration of 0.2 mM was used.

2. In vivo test (A) Anti-platelet aggregation effect in rabbits

After a Japanese white male rabbit (weight: 1.8 to 2.5 kg) was fasted for 18 hours, a test sample drug suspended in 0.5% methyl cellulose was orally administered thereto. After administration, blood was periodically collected from ear artery, and PRP was prepared in the same manner as in the above in vitro test to measure platelet aggregation caused by each aggregating agent. The effect of the test sample drug was evaluated by inhibited aggregation ratio calculated on the assumption that the aggregation before administration was 100%.

(B) Anti-platelet aggregation effect on guinea-pigs (1)After a Hartley type male guinea-pig (weight: around 350 g) was fasted for 18 hours, a test sample drug suspended in a 5% gum arabic solution was orally administered thereto. After administration, blood was collected periodically from central artery, and PRP was prepared in the same manner as in the above in vitro test to measure platelet aggregation caused by each aggregating agent. The effect of the test sample drug was evaluated by inhibited aggregation ratio calculated on the assumption that the aggregation before administration was 100%.

(2)After a Hartley type male guinea-pig (weight: around 350 g) was fasted for 18 hours, a test sample drug suspended in a 5% gum arabic solution was orally administered thereto. One hour after the administration, blood was collected from central artery, and PRP was prepared in the same manner as in the above in vitro test to measure platelet aggregation caused by each aggregating agent. The effect of the test sample drug was evaluated by inhibited aggregation ratio calculated on the assumption that the aggregation before administration was 100%.

(C) Thrombocytopenia model of mouse

Collagen (Hormon-Chemie Co., Ltd.) diluted in an isotonic sodium chloride solution was administered to an ICR male mouse (weight: 24–30 g) through the tail vein in an amount of 1 mg/5 ml/kg. Five minutes later, under pentobarbital anesthesia, 9 volume amounts of blood was collected from inferier vena cava into a plastic syringe containing one volume amount of 3.8% sodium citrate. A test sample drug was orally administered one hour before the administration of collagen. The blood thus collected was diluted 20 times with Isotone II, and was subjected to a centrifuge at 60×g for 5 minutes. Thereafter the upper layer was further diluted with Isotone II to measure the number of platelets by a coulter counter (model ZM).

In the above tests I-1 and I-2, ticlopidine hydrochloride (Daiichi Seiyaku Co., Ltd.) and Cilostazol (Otsuka Pharmaceutical Co., Ltd.) were used as control drugs.

II. Cardiotonic effect

After exsanguinating a male guinea-pig (Hartley type, 250–400 g), the heart was taken out and was immediately dipped in a nutrition solution (Kreb's-Henseleit solution: NaCl 118.4 mM, KCl 4.7 mM, $MgSO_4.7H_2O$ 1.18 mM, $CaCl_2.2H_2O$ 2.5 mM, $KH_2PO_4$ 1.2 mM, $NaHCO_3$ 24.9 mM, Glucose 11.1 mM) aerated with oxygen (containing 5% of carbon dioxide). Thereafter, the oxygen-aerated nutrition solution was placed in a laboratory dish for preparing a sample, and oxygen was continuously aerated. After rapidly separating the atrium and the ventricle, a papillary muscle sample was prepared from the right ventricle, and was suspended in an organ bath filled with the oxygen-aerated nutrition solution maintained at 31° C., then 500 mg of tension being loaded thereto.

After suspending the papillary muscle sample, the nutrition solution was replaced 20 minutes later and 40 minutes later, and after observing for further 20 minutes, isoproterenol was accumulatively administered (the final concentration: $3\times10^{-7}$M) to observe the effect on the contractile force. After repeating the procedure after suspending once more in the same manner as above, the nutrition solution was replaced 20 minutes later and 40 minutes later, and after observing for further 20 minutes, a test sample drug was accumulatively administered. The effect of each test sample drug on contractile force was evaluated by change ratio (%) caused by the test sample drug on the assumption that the difference in contractile force at the second isoproterenol administration was 100%, and a concentration $EC_{30}$ (μM) necessary for making 30% increase was calculated.

The measurement of contractile force was conducted by applying rectangular pulses [voltage: threshold value×2 (V), duration: 3 (msec), frequency: 1 (Hz)] onto the papillary muscle through bipolar platinum electrodes by an electronic stimulator (Nihon Kohden SEN-3201) to record the generated tension on a recorder by a F-D pickup and strain gage.

As a control cardiotonics, a Milrinone (Winthrop Co.) was used.

III. Vasodilatory effect

A male rabbit (Japanese white type, 2-2.5 kg) was subjected to anesthesia by intravenous injection of nembutal [weight (kg)×0.5+0.5 ml]. After exsanguination, the thoracic aorta was taken out and was immediately dipped in a nutrition solution (Kreb's-Henseleit solution: NaCl 118.4 mM, KCl 4.7 mM, $MgSO_4 \cdot 7H_2O$ 1.188 mM, $CaCl_2 \cdot 2H_2O$ 2.5 mM, $KH_2PO_4$ 1.2 mM, $NaHCO_3$ 24.9 mM, Glucose 11.1 mM) aerated with oxygen (containing 5% of carbon dioxide). Thereafter, it was placed in a laboratory dish for preparing a sample, which was filled with the oxygen-aerated nutrition solution, and both ends of the blood vessel were fixed by pins to remove fat and connective tissue. A spiral sample (width: 3 mm, length: about 1 cm) was prepared by cutting with scissors. The both sides of the sample was fixed by a clip, and was suspended in an organ bath filled with the oxygen-aerated nutrition solution and maintained at 37° C., then a tension of 2 g being loaded thereon.

The tension of the blood vessel was recorded on a recorder (Nihon Kohden) by means of an F-D pickup (Nihon Kohden 611-T) and strain gage (Nihon Kohden AP-600G).

After suspending, the nutrition solution was replaced 20 minutes later and 40 minutes later, and each sample was observed for further 20 minutes (during which the tension was maintained 2 g). Thereafter, norepinephrine was administered (final concentration: $10^{-6}M$) and the blood vessel influenced by tension was observed. After the contraction became stable, the nutrition solution was replaced, and the nutrition solution was further replaced 20 minutes later and 40 minutes later. After observing for further 20 minutes, the blood vessel was contracted by a contractile agent. After the contraction became stable, a test sample drug was accumulatively administered. After finishing the test, papaverine was administered (final concentration: $10^{-4}M$) to achieve complete relaxation.

The effect of the test sample drug on contraction by the contractile agent was evaluated by a change ratio (%) caused by the test sample drug on the assumption that the difference in tension between at the time of administration of the contractile agent and after the administration of papaverine was 100%.

IV. Anti-SRS-A effect (bronchodilating effect)

Drug

A test sample drug was used by dissolving and diluting in 100% dimethylsulfoxide (DMSO, Wako Junyaku). Leukotriene $D_4$ ($LTD_4$, Ultrafine) was diluted with distilled water.

Indomethacin (Indo, Sigma) was dissolved in 100% ethanol (EtOH, Komune Kagaku). Aminophylline (AP, Sigma), histamine dihydrochloride (His, Wako Junyaku) was dissolved in distilled water. The final concentrations of DMSO and EtOH in a bath were made respectively not higher than 0.25% v/v and not higher than 0.1% v/v.

Method

A guinea-pig of 300-450 g was exsanguinated, and the trachea was taken out. After removing fat and connective tissue, it was cut into spiral strips having a width of about 2 mm and was divided into 2 to 3 pieces, each containing 4 smooth muscle tissues. The sample thus prepared was suspended in an organ bath of 8 ml containing a modified Tyrode solution aerated with 95% $O_2$ +5% $CO_2$ at 37° C., and 1 g of load was applied thereon. The relaxation of the muscle was recorded by a pen recorder (Yokogawa Hokushin Electric, type 3066) by means of an isotonic transducer (Nihon Kohden, TD-112S).

The composition of the modified Tyrode solution was as follows (mM):

NaCl 137, KCl 2.7, $CaCl_2$ 1.8, $MgCl_2$ 1.0, $NaHCO_3$ 20, $NaH_2PO_4$ 0.32, Glucose 11.

The sample was allowed to stand for 50-60 minutes, and was contracted with histamine dihydrochloride (100 μM). After the reaction became constant, it was washed and allowed to stand for 20-30 minutes. Indomethacin (5 μM) was added to the sample, and after incubation for 30 minutes, the sample was contracted by adding $LTD_4$ (30 nM). After the reaction became stable, a test drug was accumulatively administered. Finally AP (1 mM) was added to achieve maximum relaxtant reaction. The result was expressed by relaxation percent on the assumption that the relaxation by AP was 100%, and a concentration to achieve 50% relaxation ($EC_{50}$, μM) was measured.

As a control drug, FPL-55712 recognized as a selective SRS-A antagonistic agent was used [(Fisons Ltd.); Journal of Medicinal Chemistry, Vol 20, pp. 371-379, 1977].

Test Results

I Anti-platelet aggregation effect

1. In vitro test: (A), (B)

Tables III-1 to III-3 show anti-platelet aggregation effects of test compounds evaluated as $IC_{50}$ values (μM).

TABLE III-1

| Test Compound | Rabbit PRP: $IC_{50}$ | |
|---|---|---|
| No. | ADP | A.A. |
| 1 | 0.22 | 0.5 |
| Cilostazol | 28.0 | 8.8 |

TABLE III-2

| Test Compound No. | Rabbit PRP ADP: IC$_{50}$ |
| --- | --- |
| 9 | 0.32 |
| 11 | 0.85 |
| 12 | 0.93 |
| 13 | 0.52 |
| 21 | 6.0 |
| 26 | 0.16 |
| 27 | 0.24 |
| 29 | 0.58 |
| 30 | 0.29 |
| 36 | 0.45 |
| 38 | 0.52 |
| 42 | 18.0 |
| 47 | 0.05 |
| 48 | 0.15 |
| 54 | 2.7 |
| 61 | 0.19 |
| 70 | 0.43 |
| 76 | 1.2 |
| 85 | 0.10 |
| 86 | 0.33 |
| 120 | 0.6 |
| 133 | 0.18 |
| 137 | 0.13 |
| 143 | 0.25 |
| 153 | 0.61 |
| 158 | 0.22 |
| 162 | 0.053 |
| 166 | 0.14 |
| 167 | 0.14 |
| 169 | 0.064 |
| 173 | 0.15 |
| 177 | 0.042 |
| 178 | 0.1 |
| 180 | 0.12 |
| 183 | 0.03 |
| 181 | 0.024 |
| 188 | 0.24 |
| 190 | 0.29 |
| 192 | 0.081 |
| 195 | 0.48 |
| 199 | 0.72 |
| 206 | 0.64 |
| 210 | 0.14 |
| 230 | 0.18 |
| 239 | 0.16 |
| Cilostazol | 28.0 |

TABLE III-3

| Test Compound No. | Guinea-pig PRP A.A.: IC$_{50}$ |
| --- | --- |
| 85 | 0.026 |
| 88 | 0.018 |
| 94 | 0.018 |
| 99 | 0.18 |
| Cilostazol | 1.4 |

2. in vivo test

Test III-4
(A) Anti-platelet aggregation effect in rabbits

| Test Compound No. | Administration amount (mg/kg) | Example number | Aggregation-causing agent | Average ratio of anti-platelet aggregation (%) 1 hr. | 3 hrs. |
| --- | --- | --- | --- | --- | --- |
| 72 | 50 | 2 | ADP | 57 | 59 |
| 72 | 50 | 2 | A.A. | 98 | 86 |
| 75 | 50 | 2 | ADP | 65 | 31 |
| 75 | 50 | 2 | A.A. | 76 | 21 |
| Ticlopidine hydrochloride | 300 | 3 | ADP | 24 | 36 |
| Ticlopidine hydrochloride | 300 | 3 | A.A. | 13 | 2 |

TABLE III-5

(B) Anti-platelet aggregation effect in guinea-pigs (1)

| Test Compound No. | Administration amount (mg/kg) | Example Number | Aggregation-causing agent | Average ratio of anti-platelet aggregation (%) 1 hr. | 3 hrs. |
| --- | --- | --- | --- | --- | --- |
| 166 | 10 | 3 | A.A. | 85 | 59 |
| 181 | 30 | 1 | A.A. | 69 | 71 |
| 158 | 30 | 1 | A.A. | 68 | 35 |

TABLE III-6

Anti-platelet aggregation effect in guinea pigs (2)

| Test Compound No. | Administration amount (mg/kg) | Aggregation-causing agent | Ratio of anti-platelet aggregation (%) |
| --- | --- | --- | --- |
| 85 | 3 | A.A. | 57.8 |
| 92 | 10 | A.A. | 92.5 |
| 152 | 10 | A.A. | 93.1 |
| 166 | 3 | A.A. | 93.1 |
| 181 | 10 | A.A. | 88.6 |
| 169 | 10 | A.A. | 92.7 |

TABLE III-7

(C) Effect of inhibiting reduction in platelets of mice

| Test Compound No. | Administration amount (mg/kg) | Example number | Average inhibiting ratio (%) |
| --- | --- | --- | --- |
| 38 | 30 | 5 | 31.4* |
| 52 | 30 | 5 | 51.1* |
| 84 | 10 | 5 | 55.0** |
| 85 | 30 | 5 | 36.6* |
| Ticlopidine hydrochloride | 300 | 6 | 30.1* |
| Ticlopidine hydrochloride | 100 | 6 | 13.7 |
| Cilostazol | 100 | 5 | 39.4* |
| Cilostazol | 30 | 6 | 18.3 |

*1: Significant difference from control value was statistically recognized at the ratio of risk of 5% (* mark) and at the ratio of risk of 1% (** mark).

TABLE IV

II. Cardiotonic effect

| Test Compound No. | Contractile force of heart EC$_{30}$ (μM) | Maximum reaction ratio % (μM) |
| --- | --- | --- |
| 11 | 11.2 | 57.7 (300) |
| 44 | 20.6 | 51.0 (300) |
| Milrinone | 33.9 | 59.1 (300) |

*2: Maximum contractile force is expressed by reaction rate to contractile force of isoproterenol, and numerical value in parenthesis indicates minimum concentration (measured at 300 μM) at that time.

TABLE V

| | III. Vasodilatory effect | | |
| --- | --- | --- | --- |
| | Vasodilatory effect $EC_{30}$ (μM) | | |
| Test Compound No. | NE*3 $10^{-6}$M | U-46619 $10^{-7}$M | $PGF_{2\alpha}$ $10^{-6}$M |
| 11 | 0.363 | 2.19 | 0.447 |
| Papaverine | 4.37 | 10.5 | 8.71 |

*3: NE = norepinephrine

TABLE VI

| IV. Anti-SRS-A effect | |
| --- | --- |
| Test Compound No. | $EC_{50}$ |
| 12 | 0.023 |
| 13 | 0.40 |
| 16 | 0.28 |
| 21 | 0.26 |
| 23 | 0.23 |
| 28 | 0.42 |
| 55 | 0.068 |
| 75 | 0.21 |
| 84 | 0.025 |
| 94 | 0.059 |
| 96 | 0.56 |
| FPL-55712 | 0.10 |

INDUSTRIAL APPLICABILITY

As evident from the above results, it is clear that the compound of the present invention has excellent anti-platelet aggregation effect, cardiotonic effect, vasodilatory effect and anti-SRS-A effect. Thus, the compound of the present invention can be useful prophylactic and therapeutic drugs for various thrombotic diseases, congestive heart failure, hypertension, angina pectoris, and immediate type allergy diseases including asthma.

We claim:

1. A 3(2H)-pyridazinone of the formula:

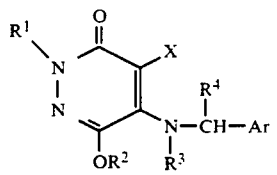

wherein $R^1$ is a hydrogen atom, a straight chain or branched $C_1$-$C_4$ alkyl group, a $C_3$-$C_4$ alkenyl group or $(CH_2)_n CO_2 R^5$ (where n is an integer from 1 to 4, $R^5$ is a hydrogen atom or a straight chain or branched $C_1$-$C_4$ alkyl group;

$R^2$ is $A^1$-$Y^1$ (where $A^1$ is a straight chain or branched $C_1$-$C_{12}$ alkylene group, $Y^1$ is $CO_2R^5$, a cyano group, $OR^6$ (where $R^6$ is a hydrogen atom, a straight chain or branched $C_1$-$C_4$ alkyl group or a phenyl group),

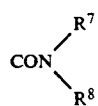

(where $R^7$ and $R^8$ are independently a hydrogen atom, a straight chain or branched $C_1$-$C_4$ alkyl group, a $C_3$-$C_8$ cycloalkyl group, a phenyl group or a thiazolyl or thiadiazolyl group which is unsubstituted or substituted at any position, or $R^7$ and $R^8$ together form a $C_2$-$C_8$ alkylene group which is unsubstituted or substituted with a straight chain or branched $C_1$-$C_3$ alkyl group or a phenyl group, or form a morpholine ring with a nitrogen atom),

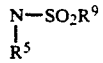

(where $R^5$ is as defined above and $R^9$ is a straight chain or branched $C_1$-$C_4$ alkyl group or a phenyl group which is unsubstituted or substituted with a straight chain or branched $C_1$-$C_4$ alkyl group or a halogen atom),

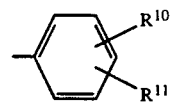

(where $R^{10}$ and $R^{11}$ are independently a hydrogen atom, a halogen atom, a straight chain or branched $C_1$-$C_4$ alkyl group, a $C_1$-$C_4$ acylamino group, $OR^5$, $NHSO_2R^9$ or $S(O)_m$-$R^{12}$ (where m is an integer from 0 to 2 and $R^{12}$ is a straight chain or branched $C_1$-$C_4$ alkyl group), provided that $R^{10}$ and $R^{11}$ are not hydrogen atoms at the same time),

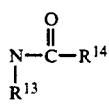

(where $R^{13}$ is a hydrogen atom and $R^{14}$ is a phenyl group, or $R^{13}$ and $R^{14}$ together form a $C_2$-$C_8$ alkylene group which is unsubstituted or substituted with a straight chain $C_1$-$C_3$ alkyl group),

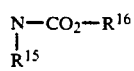

(where $R^{15}$ is a hydrogen atom or a straight chain or branched $C_1$-$C_4$ alkyl group, $R^{16}$ is a straight chain or branched $C_1$-$C_4$ alkyl group, or $R^{15}$ and $R^{16}$ together form a $C_2$-$C_8$ alkylene group which is unsubstituted or substituted with a straight chain $C_1$-$C_3$ alkyl group),

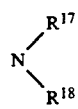

(where $R^{17}$ and $R^{18}$ are independently a straight chain or branched $C_1$-$C_4$ alkyl group, or $R^{17}$ and $R^{18}$ together form a $C_2$-$C_8$ alkylene group which is unsubstituted or substituted with a straight chain $C_1$-$C_3$ alkyl group),

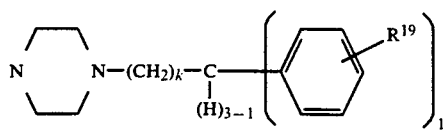

(where l is 1 or 2, k is an integer from 0 to 3, and $R^{19}$ is a hydrogen atom or a halogen atom), or

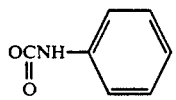

) or $R^2$ is $A^2$-$Y^2$ (where $A^2$ is a $C_2$-$C_{10}$ alkylene group which is unsubstituted or substituted with a straight chain $C_1$-$C_3$ alkyl group, except where a carbon chain connecting an oxygen atom with $Y^2$ has one carbon, and $Y^2$ is a phenyl group);

$R^3$ and $R^4$ are independently a hydrogen atom or a straight chain or branched $C_1$-$C_3$ alkyl group;

X is a chlorine atom, a bromine atom, a hydrogen atom or a cyano group; and

Ar is

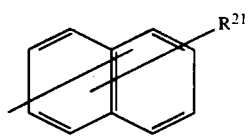

where $R^{21}$ is a hydrogen atom or $OR^5$ (where $R^5$ is as defined above), or

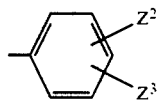

(where $Z^2$ and $Z^3$ are independently a hydrogen atom, a halogen atom, a straight chain or branched $C_1$-$C_4$ alkyl group, $OR^{22}$ (where $R^{22}$ is a hydrogen atom or a straight chain or branched $C_1$-$C_8$ alkyl group), or O—$A^1$—$Y^3$ (where $A^1$ is as defined above and $Y^3$ is a phenyl group which is unsubstituted or substituted with a straight chain or branched $C_1$-$C_4$ alkyl group or a halogen atom, $CO_2R^5$, or

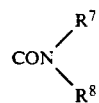

(where $R^5$, $R^7$ and $R^8$ are as defined above)), or $Z^2$ and $Z^3$ together with a benzene ring, form

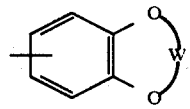

(where W is a $C_1$-$C_8$ alkylene group which is unsubstituted or substituted with a straight chain $C_1$-$C_3$ alkyl group)); or a pharmaceutically acceptable salt thereof.

2. The 3(2H)-pyridazinone compound according to claim 1, wherein $R^4$ is a hydrogen atom and X is a chlorine atom, a bromine atom or a cyano group; and a pharmaceutically acceptable salt thereof.

3. The 3(2H)-pyridazinone compound and the pharmaceutically acceptable salt thereof according to claim 2, wherein $R^1$ and $R^3$ are hydrogen atoms.

4. The 3(2H)-pyridazinone compound according to claim 2 of the formula:

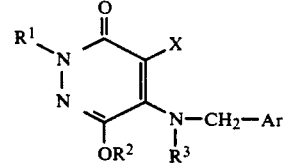

wherein $R^1$ is a hydrogen atom, a straight chain or branched $C_1$-$C_4$ alkyl group, or $(CH_2)_nCO_2R^4$ (where n is an integer from 1 to 4, $R^4$ is a hydrogen atom or a straight chain or branched $C_1$-$C_4$ alkyl group;

$R^2$ is $A^1$-$Y^1$ (where $A^1$ is a straight chain or branched $C_1$-$C_{12}$ alkylene group, $Y^1$ is $CO_2R^4$, a cyano group, a phenoxy group

(where $R^5$ and $R^6$ are independently a hydrogen atom, a straight chain or branched $C_1$-$C_4$ alkyl group, a $C_3$-$C_8$ cycloalkyl group, a phenyl group or a thiazolyl or thiadiazolyl group which is unsubstituted or substituted at any position, or $R^5$ and $R^6$ together form a $C_2$-$C_8$ alkylene group which is unsubstituted or substituted with a straight chain or branched $C_1$-$C_3$ alkyl group or a phenyl group, or form a morpholine ring with a nitrogen atom), $$N-SO_2R^7$$
$$|$$
$$R^4$$

(where $R^4$ is as defined above, $R^7$ is a straight chain or branched $C_1$-$C_4$ alkyl group or a phenyl group which is unsubstituted or substituted with a halogen atom),

(where $R^8$ and $R^9$ are independently a hydrogen atom, a halogen atom, a straight chain or branched $C_1$-$C_4$ alkyl group, a $C_1$-$C_4$ acylamino group, $OR^4$, $NHSO_2R^{10}$ ($R^{10}$ is a straight chain or branched $C_1$-$C_4$ alkyl group) or $S(O)_m$-$R^{10}$ (where m is an integer from 0 to 2 and $R^{10}$ is as defined above) provided that $R^8$ and $R^9$ are not hydrogen atoms at the same time),

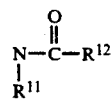

(where $R^{11}$ is a hydrogen atom, $R^{12}$ is a phenyl group, or $R^{11}$ and $R^{12}$ together form a $C_2-C_5$ alkylene group,

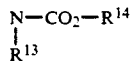

(where $R^{13}$ is a hydrogen atom or a straight chain or branched $C_1-C_4$ alkyl group, $R^{14}$ is a straight chain or branched $C_1-C_4$ alkyl group, or $R^{13}$ and $R^{14}$ together form a $C_1-C_4$ alkylene group,

(where $R^{15}$ and $R^{16}$ are independently a straight chain or branched $C_1-C_4$ alkyl group, or $R^{15}$ and $R^{16}$ together form a $C_2-C_6$ alkylene group,

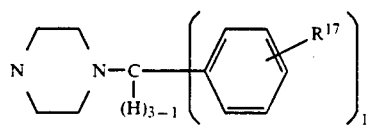

(where l is 1 or 2, $R^{17}$ is a hydrogen atom or a halogen atom), or

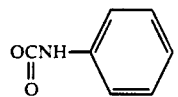

) or $R^2$ is $A^2-Y^2$ (where $A^2$ is a $C_2-C_8$ alkylene group which is unsubstituted or substituted with a straight chain $C_1-C_3$ alkyl group, except where a carbon chain connecting an oxygen atom with $Y^2$ has one carbon, and $Y^2$ is a phenyl group);

$R^3$ is a hydrogen atom or a straight chain or branched $C_1-C_3$ alkyl group;

X is a chlorine atom, a bromine atom, or a cyano group; and

Ar is

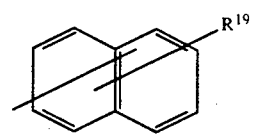

where $R^{19}$ is a hydrogen atom or $OR^4$ (where $R^4$ is as defined above), or

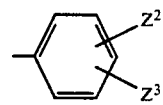

(where $Z^2$ and $Z^3$ are independently a hydrogen atom, a halogen atom, a straight chain or branched $C_1-C_4$ alkyl group, $OR^{20}$ (where $R^{20}$ is a hydrogen atom or a straight chain or branched $C_1-C_8$ alkyl group), or $O-A^3-Y^3$ (where $A^3$ is a $C_1-C_4$ alkylene group and $Y^3$ is a phenyl group, $CO_2R^4$, or

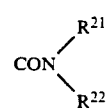

(where $R^{21}$ and $R^{22}$ are independently a straight chain or branched $C_1-C_4$ alkyl group or a $C_3-C_7$ cycloalkyl group, or $R^{21}$ and $R^{22}$ together form a $C_2-C_6$ alkylene group), or $Z^2$ and $Z^3$ together with a benzene ring, form

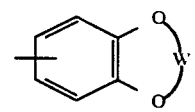

(where W is a $C_1-C_2$ alkylene group); or a pharmaceutically acceptable salt thereof.

5. An anti-thrombotic agent containing the 3(2H)-pyridazinone compound and its pharmaceutically acceptable salt as defined in claim 1 as an effective ingredient.

6. An inotropic agent containing the 3(2H)-pyridazinone compound and its pharmaceutically acceptable salt as defined in claim 1 as an effective ingredient.

7. A vasodilatory agent containing the 3(2H)-pyridazinone compound and its pharmaceutically acceptable salt as defined in claim 1 as an effective ingredient.

8. An anti-SRS-A agent containing the 3(2H)-pyridazinone compound and its pharmaceutically acceptable salt as defined in claim 1 as an effective ingredient.

* * * * *